(12) United States Patent
Stanimirovic et al.

(10) Patent No.: US 8,986,689 B2
(45) Date of Patent: Mar. 24, 2015

(54) COMPOSITIONS AND METHODS FOR BRAIN DELIVERY OF ANALGESIC PEPTIDES

(75) Inventors: Danica Stanimirovic, Ottawa (CA); Abedelnasser Abulrob, Ottawa (CA); Eric Brunette, Orleans (CA); Nadia Caram-Salas, Ottawa (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 13/640,842

(22) PCT Filed: Apr. 13, 2011

(86) PCT No.: PCT/CA2011/000416
§ 371 (c)(1),
(2), (4) Date: Oct. 12, 2012

(87) PCT Pub. No.: WO2011/127580
PCT Pub. Date: Oct. 20, 2011

(65) Prior Publication Data
US 2013/0034572 A1    Feb. 7, 2013

Related U.S. Application Data

(60) Provisional application No. 61/324,036, filed on Apr. 14, 2010.

(51) Int. Cl.
| A61K 39/00 | (2006.01) |
| A61K 39/395 | (2006.01) |
| C07K 16/00 | (2006.01) |
| C07K 14/575 | (2006.01) |
| A61K 47/48 | (2006.01) |

(52) U.S. Cl.
CPC ..... *C07K 14/57545* (2013.01); *A61K 47/48415* (2013.01); *A61K 47/48561* (2013.01)
USPC .............. 424/134.1; 424/130.1; 424/178.1; 530/387.1; 530/387.3; 530/391.7

(58) Field of Classification Search
None
See application file for complete search history.

(56) References Cited

U.S. PATENT DOCUMENTS

| 5,693,761 A | 12/1997 | Queen et al. |
| 5,766,886 A | 6/1998 | Studnicka et al. |
| 5,821,123 A | 10/1998 | Studnicka |
| 5,859,205 A | 1/1999 | Adair et al. |
| 5,869,619 A | 2/1999 | Studnicka |
| 6,054,297 A | 4/2000 | Carter et al. |
| 6,180,370 B1 | 1/2001 | Queen et al. |

FOREIGN PATENT DOCUMENTS

| EP | 0519596 | 2/2005 |
| EP | 0626390 | 11/2011 |
| WO | 02057445 | 7/2002 |
| WO | 2007036021 | 4/2007 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Ulbrich K et al., Transferrin- and trasnferrin-receptor-antibody-modified nanoparticles enable drug delivery across the blood-brain barrier (BBB), European Journal of Pharmaceutics and Biopharmaceutics, vol. 71, No. 2, 2009, pp. 251-256.
Abulrob A et al., Single domain antibodies as blood-brain barrier delivery vectors, International Congress Series, Excerpta Medica, vol. 1277, Apr. 2005 pp. 212-223.
Extended European Search Report issued Dec. 20, 2013 for corresponding European Application No. 11768320.1.
Balasubramaniam AA. (1997) Neuropeptide Y family of hormones: receptor subtypes and antagonsts. Peptides. 18(3):445-57.
Baraban SC: Neuropeptide Y and epilepsy: recent progress,prospects and controversies. Neuropeptides 38:261-265, 2004.
Bickel, U., Yoshikawa, T., & Pardridge, W.M. Delivery of peptides and proteins through the blood-brain barrier. Adv. Drug Deliv. Rev. 46, 247-279 (2001).
Demeule M, Currie JC, Bertrand Y, Ché C, Nguyen T, Régina A, Gabathuler R, Castaigne JP, Béliveau R. Involvement of the low-density lipoprotein receptor-related protein in the transcytosis of the brain delivery vector angiopep-2. J Neurochenn. 106(4):1534-44. (2008).
Eisenberg et al. Analysis of membrane and surface protein sequences with the hydrophobic moment plot. J. Mol. Biol., 179, 125-142, (1984).
Garberg P, Ball M, Borg N, Cecchelli R, Fenart L, Hurst RD, Lindmark T, Mabondzo A, Nilsson JE, Raub TJ, Stanimirovic D, Terasaki T, Oberg JO, Osterberg T. In vitro models for the blood-brain barrier. Toxicol In Vitro. 19(3):299-334 (2005).

(Continued)

*Primary Examiner* — Christine J Saoud
*Assistant Examiner* — Jon M Lockard
(74) *Attorney, Agent, or Firm* — Sonia Patenaude

(57) ABSTRACT

The present invention relates to non-invasive brain delivery technology for centrally-acting analgesic peptides. Specifically, the invention is directed to compounds comprising an antibody or fragment thereof capable of transmigrating across the blood brain barrier (BBB) and an analgesic peptide. Compositions and methods of using the compounds or compositions are also provided.

7 Claims, 11 Drawing Sheets

(56) References Cited

OTHER PUBLICATIONS

Hamers-Casterman, C. et al. Naturally occurring antibodies devoid of light chains. Nature 363, 446-448 (1993).

Hervé F, Ghinea N, Scherrmann JM. CNS delivery via adsorptive transcytosis. AAPS J.10(3):455-72. (2008).

Jespers, L., Schon, O., Famm, K. & Winter, G. Aggregation-resistant domain antibodies selected on phage by heat denaturation. Nat Biotechnol 22, 1161-1165 (2004).

Jones AR, Shusta EV. Blood-brain barrier transport of therapeutics via receptor-mediation. Pharm Res. 24(9):1759-71 (2007).

Kabat EA, Wu TT. Identical V region amino acid sequences and segments of sequences in antibodies of different specificities. Relative contributions of VH and VL genes, minigenes, and complementarity-determining regions to binding of antibody-combining sites. J Immunol. 1991;147:1709-19.

Munglani R, Hudspith MJ, Hunt SP (1996) The therapeutic potential of neuropeptide Y. Analgesic, anxiolytic and antihypertensive. Drugs. 52(3):371-89.

Murriel CL, Dowdy SF. Influence of protein transduction domains on intracellular delivery of macromolecules. Expert Opin Drug Deliv. 3(6):739-46.(2006).

Muruganandam A, Tanha J, Narang S, Stanimirovic D. Selection of phage-displayed llama single-domain antibodies that transmigrate across human blood-brain barrier endothelium. FASEB J. 16(2):240-2. (2002).

Niederberger E, Kühlein H, Geisslinger G. Update on the pathobiology of neuropathic pain. Expert Rev Proteomics. 5(6):799-818 (2008).

Nuttall, S.D. et al. Isolation and characterization of an IgNAR variable domain specific for the human mitochondrial translocase receptor Tom70. European journal of biochemistry / FEBS 270, 3543-3554 (2003).

Padlan, E.A. Anatomy of the antibody molecule. Molecular immunology 31, 169-217 (1994).

Pardridge, W.M. Drug and gene delivery to the brain: The vascular route. Neuron 36:555-558 (2002).

Pardridge, W.M., Buciak, J.L., & Friden, P.M. Selective transport of an anti-transferrin receptor antibody through the blood-brain barrier in vivo. J. Pharmacol. Exp. Ther. 259, 66-70 (1991).

Pencheva N, Pospisek J, Hauzerova L, Barth T, Milanov P. Activity profiles of dalargin and its analogues in mu-, delta-and kappa-opioid receptor selective bioassays. Br J Pharmacol. 128(3):569-76 (1999).

Polt R, Dhanasekaran M, Keyari CM. Glycosylated neuropeptides: a new vista for neuropsychopharmacology? Med Res Rev. 25(5):557-85 (2005).

Redrobe JP, Dumont Y, St-Pierre J-A, Quirion R: Multiple receptors for neuropeptide Y in the hippocampus: putative roles in seizures and cognition Brain Research 848:153-166, 1999.

Rousselle C, Clair P, Smirnova M, Kolesnikov Y, Pasternak GW, Gac-Breton S, Rees AR, Scherrmann JM, Temsamani J. Improved brain uptake and pharmacological activity of dalargin using a peptide-vector-mediated strategy. J Pharmacol Exp Ther 306(1):371-6 (2003).

Smith HS. Peripherally-acting opioids. Pain Physician. 11(2 Suppl):S121-32. (2008).

To, R. et al. Isolation of monomeric human V(H)s by a phage selection. J Biol Chem 280, 41395-41403 (2005).

Trescot AM, Datta S, Lee M, Hansen H. Opioid pharmacology. Pain Physician. 11(2 Suppl):S133-53 (2008).

Vezzani A, Sperk G: Overexpression of NPY and Y2 receptors in epileptic brain tissue: an endogenous neuroprotective mechanism in temporal lobe epilepsy? Neuropeptides 38: 245-252, 2004.

Weber, S. J., Greene, D. L., Sharma, S. D., Yamamura, H. I., Kramer, T. H., Burks, T. F., Hruby, J. H., Hersh, L. B. and Davis, T. P.: Distribution and antinociception of [3H]cyclic [D-Pen2, D-Pen5]enkephalin and two halogenated analogs after intravenous administration. J. Pharmacol. Exp. Ther. 259: 1109-1117, 1991.

Woldbye DP, Larsen PJ, Mikkelsen JD, Klemp K, Madsen TM, Bolwig TG. Powerful inhibition of kainic acid seizures by neuropeptide Y via Y5-like receptors. Nat Med. 3(7):761-4, 1997.

Woldbye DPD: Antiepileptic effects of NPY on pentylenetetrazole seizures. Regulatory Peptides 75-76:279-282, 1998.

Xapelli S, Agasse F, Ferreira R, Silva AP, Malva JO.: Neuropeptide Y as an endogenous antiepileptic, neuroprotective and pro-neurogenic peptide. Recent Pat CNS Drug Discov.;1(3):315-24, 2006.

PCT IPRP for PCT/CA2011/000416, Oct. 2012.

PCT ISR for PCT/CA2011/000416, Jun. 2011.

PCT Written Opinion for PCT/CA2011/000416, Jun. 2011.

\* cited by examiner

SEQUENCE LISTING

```
<160> NUMBER OF SEQ ID NOS: 14

<210> SEQ ID NO 1
<211> LENGTH: 5
<212> TYPE: PRT
<213> ORGANISM: artificial sequence
<220> FEATURE:
<223> OTHER INFORMATION: CDR1

<400> SEQUENCE: 1

His Tyr Thr Met Gly
1               5

<210> SEQ ID NO 2
<211> LENGTH: 17
<212> TYPE: PRT
<213> ORGANISM: artificial sequence
<220> FEATURE:
<223> OTHER INFORMATION: CDR2

<400> SEQUENCE: 2

Arg Ile Thr Trp Gly Gly Asp Asn Thr Phe Tyr Ser Asn Ser Val Lys
1               5                   10                  15

Gly

<210> SEQ ID NO 3
<211> LENGTH: 13
<212> TYPE: PRT
<213> ORGANISM: artificial sequence
<220> FEATURE:
<223> OTHER INFORMATION: CDR3

<400> SEQUENCE: 3

Gly Ser Thr Ser Thr Ala Thr Pro Leu Arg Val Asp Tyr
1               5                   10

<210> SEQ ID NO 4
<211> LENGTH: 122
<212> TYPE: PRT
<213> ORGANISM: artificial sequence
<220> FEATURE:
<223> OTHER INFORMATION: FC5 sdAb

<400> SEQUENCE: 4

Glu Val Gln Leu Gln Ala Ser Gly Gly Gly Leu Val Gln Ala Gly Gly
1               5                   10                  15

Ser Leu Arg Leu Ser Cys Ala Ala Ser Gly Phe Lys Ile Thr His Tyr
                20                  25                  30

Thr Met Gly Trp Phe Arg Gln Ala Pro Gly Lys Glu Arg Glu Phe Val
            35                  40                  45

Ser Arg Ile Thr Trp Gly Gly Asp Asn Thr Phe Tyr Ser Asn Ser Val
        50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Asp Tyr Tyr Cys
                 85                  90                  95

Ala Ala Gly Ser Thr Ser Thr Ala Thr Pro Leu Arg Val Asp Tyr Trp
            100                 105                 110

Gly Lys Gly Thr Gln Val Thr Val Ser Ser
        115                 120

<210> SEQ ID NO 5
<211> LENGTH: 6
<212> TYPE: PRT
<213> ORGANISM: artificial sequence
<220> FEATURE:
<223> OTHER INFORMATION: Dalargin
<220> FEATURE:
<221> NAME/KEY: D-Asp
<222> LOCATION: (2)..(2)

<400> SEQUENCE: 5

Tyr Xaa Gly Phe Leu Arg
1               5

<210> SEQ ID NO 6
<211> LENGTH: 97
<212> TYPE: PRT
<213> ORGANISM: artificial sequence
<220> FEATURE:
<223> OTHER INFORMATION: Neuropeptide Y

<400> SEQUENCE: 6

Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
                20                  25                  30

Pro Asp Asn Pro Gly Glu Asp Ala Pro Ala Glu Asp Met Ala Arg Tyr
            35                  40                  45

Tyr Ser Ala Leu Arg His Tyr Ile Asn Leu Ile Thr Arg Gln Arg Tyr
        50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp

<210> SEQ ID NO 7
<211> LENGTH: 36
<212> TYPE: PRT
<213> ORGANISM: artificial sequence
<220> FEATURE:
<223> OTHER INFORMATION: Neuropeptide Y fragment

<400> SEQUENCE: 7

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
                20                  25                  30

Arg Gln Arg Tyr
        35

<210> SEQ ID NO 8
<211> LENGTH: 30
<212> TYPE: DNA
<213> ORGANISM: artificial sequence
```

<220> FEATURE:
<223> OTHER INFORMATION: fdTGIII primer

<400> SEQUENCE: 8
gtgaaaaaat tattattatt cgcaattcct                              30

<210> SEQ ID NO 9
<211> LENGTH: 20
<212> TYPE: DNA
<213> ORGANISM: artificial sequence
<220> FEATURE:
<223> OTHER INFORMATION: 96GIII primer

<400> SEQUENCE: 9
ccctcatagt tagcgtaacg                                         20

<210> SEQ ID NO 10
<211> LENGTH: 366
<212> TYPE: DNA
<213> ORGANISM: artificial sequence
<220> FEATURE:
<223> OTHER INFORMATION: FC5 sdAb

<400> SEQUENCE: 10
gaggtccagc tgcaggcgtc tggaggagga ttggtgcagg ctgggggctc tctgagactc       60
tcctgtgcag cctctggatt caaaatcact cactatacca tgggctggtt ccgccaggct      120
ccagggaagg agcgtgaatt tgtatcacgt attacttggg gtggtgataa caccttctat      180
tcaaactccg tgaagggccg attcaccatt tccagagaca cgccaagaa cacggtctat       240 ctgcaaatga acagcctgaa acctgaggac acggccgatt attactgtgc agcaggttcg      300
acgtcgactg cgacgccact tagggtggac tactggggca aaggagcccca ggtcaccgtc      360 tcctca                                                                366

<210> SEQ ID NO 11
<211> LENGTH: 361
<212> TYPE: PRT
<213> ORGANISM: artificial sequence
<220> FEATURE:
<223> OTHER INFORMATION: TMEM30A isoform 1

<400> SEQUENCE: 11

Met Ala Met Asn Tyr Asn Ala Lys Asp Glu Val Asp Gly Gly Pro Pro
1               5                   10                  15

Cys Ala Pro Gly Gly Thr Ala Lys Thr Arg Arg Pro Asp Asn Thr Ala
            20                  25                  30

Phe Lys Gln Gln Arg Leu Pro Ala Trp Gln Pro Ile Leu Thr Ala Gly
        35                  40                  45

Thr Val Leu Pro Ile Phe Phe Ile Ile Gly Leu Phe Ile Pro Ile
    50                  55                  60

Gly Ile Gly Ile Phe Val Thr Ser Asn Asn Ile Arg Glu Ile Glu Ile
65                  70                  75                  80

Asp Tyr Thr Gly Thr Glu Pro Ser Ser Pro Cys Asn Lys Cys Leu Ser
                85                  90                  95

Pro Asp Val Thr Pro Cys Phe Cys Thr Ile Asn Phe Thr Leu Glu Lys
            100                 105                 110

Ser Phe Glu Gly Asn Val Phe Met Tyr Tyr Gly Leu Ser Asn Phe Tyr
        115                 120                 125

Gln Asn His Arg Arg Tyr Val Lys Ser Arg Asp Asp Ser Gln Leu Asn
    130                 135                 140

Gly Asp Ser Ser Ala Leu Leu Asn Pro Ser Lys Glu Cys Glu Pro Tyr
145                 150                 155                 160

Arg Arg Asn Glu Asp Lys Pro Ile Ala Pro Cys Gly Ala Ile Ala Asn
            165                 170                 175

Ser Met Phe Asn Asp Thr Leu Glu Leu Phe Leu Leu Gly Asn Asp Ser
        180                 185                 190

Tyr Pro Ile Pro Ile Ala Leu Lys Lys Gly Ile Ala Trp Trp Thr
    195                 200                 205

Asp Lys Asn Val Lys Phe Arg Asn Pro Gly Gly Asp Asn Leu Glu
    210                 215                 220

Glu Arg Phe Lys Gly Thr Thr Lys Pro Val Asn Trp Leu Lys Pro Val
225                 230                 235                 240

Tyr Met Leu Asp Ser Asp Pro Asp Asn Asn Gly Phe Ile Asn Glu Asp
            245                 250                 255

Phe Ile Val Trp Met Arg Thr Ala Ala Leu Pro Thr Phe Arg Lys Leu
        260                 265                 270

Tyr Arg Leu Leu Glu Arg Lys Ser Asp Leu His Pro Thr Leu Pro Ala
    275                 280                 285

Gly Arg Tyr Ser Leu Asn Val Thr Tyr Asn Tyr Pro Val His Tyr Phe
290                 295                 300

Asp Gly Arg Lys Arg Met Ile Leu Ser Thr Ile Ser Trp Met Gly Gly
305                 310                 315                 320

Lys Asn Pro Phe Leu Gly Ile Ala Tyr Ile Ala Val Gly Ser Ile Ser
            325                 330                 335

Phe Leu Leu Gly Val Val Leu Leu Val Ile Asn His Lys Tyr Arg Asn
        340                 345                 350

Ser Ser Asn Thr Ala Asp Ile Thr Ile
    355                 360

<210> SEQ ID NO 12
<211> LENGTH: 325
<212> TYPE: PRT
<213> ORGANISM: artificial sequence
<220> FEATURE:
<223> OTHER INFORMATION: TMEM30A isoform 2

<400> SEQUENCE: 12

Met Ala Met Asn Tyr Asn Ala Lys Asp Glu Val Asp Gly Gly Pro Pro
1               5                   10                  15

Cys Ala Pro Gly Gly Thr Ala Lys Thr Arg Arg Pro Asp Asn Thr Ala
            20                  25                  30

Phe Lys Gln Gln Arg Leu Pro Ala Trp Gln Pro Ile Leu Thr Ala Gly
        35                  40                  45

Thr Val Leu Pro Ile Phe Phe Ile Ile Gly Leu Leu Phe Ile Pro Ile
    50                  55                  60

Gly Ile Gly Ile Phe Val Thr Ser Asn Ile Arg Glu Ile Glu Gly
65                  70                  75                  80

Asn Val Phe Met Tyr Tyr Gly Leu Ser Asn Phe Tyr Gln Asn His Arg
            85                  90                  95

Arg Tyr Val Lys Ser Arg Asp Asp Ser Gln Leu Asn Gly Asp Ser Ser
        100                 105                 110

Ala Leu Leu Asn Pro Ser Lys Glu Cys Glu Pro Tyr Arg Arg Asn Glu
    115                 120                 125

Asp Lys Pro Ile Ala Pro Cys Gly Ala Ile Ala Asn Ser Met Phe Asn
130                 135                 140

-continued

```
Asp Thr Leu Glu Leu Phe Leu Leu Gly Asn Asp Ser Tyr Pro Ile Pro
145                 150                 155                 160

Ile Ala Leu Lys Lys Lys Gly Ile Ala Trp Trp Thr Asp Lys Asn Val
                165                 170                 175

Lys Phe Arg Asn Pro Pro Gly Gly Asp Asn Leu Glu Glu Arg Phe Lys
            180                 185                 190

Gly Thr Thr Lys Pro Val Asn Trp Leu Lys Pro Val Tyr Met Leu Asp
        195                 200                 205

Ser Asp Pro Asp Asn Asn Gly Phe Ile Asn Glu Asp Phe Ile Val Trp
    210                 215                 220

Met Arg Thr Ala Ala Leu Pro Thr Phe Arg Lys Leu Tyr Arg Leu Leu
225                 230                 235                 240

Glu Arg Lys Ser Asp Leu His Pro Thr Leu Pro Ala Gly Arg Tyr Ser
                245                 250                 255

Leu Asn Val Thr Tyr Asn Tyr Pro Val His Tyr Phe Asp Gly Arg Lys
            260                 265                 270

Arg Met Ile Leu Ser Thr Ile Ser Trp Met Gly Gly Lys Asn Pro Phe
        275                 280                 285

Leu Gly Ile Ala Tyr Ile Ala Val Gly Ser Ile Ser Phe Leu Leu Gly
    290                 295                 300

Val Val Leu Leu Val Ile Asn His Lys Tyr Arg Asn Ser Ser Asn Thr
305                 310                 315                 320

Ala Asp Ile Thr Ile
                325

<210> SEQ ID NO 13
<211> LENGTH: 242
<212> TYPE: PRT
<213> ORGANISM: artificial sequence
<220> FEATURE:
<223> OTHER INFORMATION: TMEM30A isoform 3

<400> SEQUENCE: 13

Met Tyr Tyr Gly Leu Ser Asn Phe Tyr Gln Asn His Arg Arg Tyr Val
1               5                   10                  15

Lys Ser Arg Asp Asp Ser Gln Leu Asn Gly Asp Ser Ser Ala Leu Leu
            20                  25                  30

Asn Pro Ser Lys Glu Cys Glu Pro Tyr Arg Arg Asn Glu Asp Lys Pro
        35                  40                  45

Ile Ala Pro Cys Gly Ala Ile Ala Asn Ser Met Phe Asn Asp Thr Leu
    50                  55                  60

Glu Leu Phe Leu Leu Gly Asn Asp Ser Tyr Pro Ile Pro Ile Ala Leu
65                  70                  75                  80

Lys Lys Lys Gly Ile Ala Trp Trp Thr Asp Lys Asn Val Lys Phe Arg
                85                  90                  95

Asn Pro Pro Gly Gly Asp Asn Leu Glu Glu Arg Phe Lys Gly Thr Thr
            100                 105                 110

Lys Pro Val Asn Trp Leu Lys Pro Val Tyr Met Leu Asp Ser Asp Pro
        115                 120                 125

Asp Asn Asn Gly Phe Ile Asn Glu Asp Phe Ile Val Trp Met Arg Thr
    130                 135                 140

Ala Ala Leu Pro Thr Phe Arg Lys Leu Tyr Arg Leu Ile Glu Arg Lys
145                 150                 155                 160

Ser Asp Leu His Pro Thr Leu Pro Ala Gly Arg Tyr Ser Leu Asn Val
                165                 170                 175
```

```
Thr Tyr Asn Tyr Pro Val His Tyr Phe Asp Gly Arg Lys Arg Met Ile
                180                 185                 190

Leu Ser Thr Ile Ser Trp Met Gly Gly Lys Asn Pro Phe Leu Gly Ile
            195                 200                 205

Ala Tyr Ile Ala Val Gly Ser Ile Ser Phe Leu Leu Gly Val Val Leu
        210                 215                 220

Leu Val Ile Asn His Lys Tyr Arg Asn Ser Ser Asn Thr Ala Asp Ile
225                 230                 235                 240

Thr Ile

<210> SEQ ID NO 14
<211> LENGTH: 257
<212> TYPE: PRT
<213> ORGANISM: artificial sequence
<220> FEATURE:
<223> OTHER INFORMATION: TMEM30A extracellular domain

<400> SEQUENCE: 14

Gly Ile Phe Val Thr Ser Asn Asn Ile Arg Glu Ile Glu Ile Asp Tyr
1               5                   10                  15

Thr Gly Thr Glu Pro Ser Ser Pro Cys Asn Lys Cys Leu Ser Pro Asp
            20                  25                  30

Val Thr Pro Cys Phe Cys Thr Ile Asn Phe Thr Leu Glu Lys Ser Phe
        35                  40                  45

Glu Gly Asn Val Phe Met Tyr Tyr Gly Leu Ser Asn Phe Tyr Gln Asn
    50                  55                  60

His Arg Arg Tyr Val Lys Ser Arg Asp Asp Ser Gln Leu Asn Gly Asp
65                  70                  75                  80

Ser Ser Ala Leu Leu Asn Pro Ser Lys Glu Cys Glu Pro Tyr Arg Arg
                85                  90                  95

Asn Glu Asp Lys Pro Ile Ala Pro Cys Gly Ala Ile Ala Asn Ser Met
            100                 105                 110

Phe Asn Asp Thr Leu Glu Leu Phe Leu Leu Gly Asn Asp Ser Tyr Pro
        115                 120                 125

Ile Pro Ile Ala Leu Lys Lys Lys Gly Ile Ala Trp Trp Thr Asp Lys
130                 135                 140

Asn Val Lys Phe Arg Asn Pro Pro Gly Gly Asp Asn Leu Glu Glu Arg
145                 150                 155                 160

Phe Lys Gly Thr Thr Lys Pro Val Asn Trp Leu Lys Pro Val Tyr Met
                165                 170                 175

Leu Asp Ser Asp Pro Asp Asn Asn Gly Phe Ile Asn Glu Asp Phe Ile
            180                 185                 190

Val Trp Met Arg Thr Ala Ala Leu Pro Thr Phe Arg Lys Leu Tyr Arg
        195                 200                 205

Leu Leu Glu Arg Lys Ser Asp Leu His Pro Thr Leu Pro Ala Gly Arg
    210                 215                 220

Tyr Ser Leu Asn Val Thr Tyr Asn Tyr Pro Val His Tyr Phe Asp Gly
225                 230                 235                 240

Arg Lys Arg Met Ile Leu Ser Thr Ile Ser Trp Met Gly Gly Lys Asn
                245                 250                 255

Pro
```

COMPOSITIONS AND METHODS FOR BRAIN DELIVERY OF ANALGESIC PEPTIDES

This application is a national entry of International Patent Application PCT/CA2011/000416 filed Apr. 13, 2011 and claims the benefit of U.S. Provisional Patent Application U.S. Ser. No. 61/324,036 filed Apr. 14, 2010, the entire contents of both of which are hereby incorporated by reference.

FIELD OF THE INVENTION

The present invention relates to compositions and methods for brain delivery of peptides. More specifically, the present invention relates to non-invasive brain delivery technology for centrally-acting analgesic peptides.

BACKGROUND OF THE INVENTION

The blood-brain barrier (BBB) is formed by the brain capillary endothelial cells and acts as a selective partition regulating the exchange of substances between the blood and the brain. The tight junctions of brain capillary endothelial cells prevent a majority of circulating compounds larger than 500D from reaching the brain by the paracellular route (Pardridge, 2002). Similarly, virtually no peptides, antibodies or biologics can cross the BBB in therapeutically relevant concentrations (Pardridge, 2002; Bickel et al, 2001).

There is currently no clinically approved/used approach to deliver biologics, including peptides, across the BBB after systemic injection. At present, biologics that do not cross the BBB can only be given by direct intra-cerebroventricular or intra-brain injection, by infusion through a brain-implanted pump, or by implantation of controlled-release polymers or genetically engineered cells. There are some experimental approaches that are being developed for systemic delivery of biologics, such as peptides, across the BBB including: development of highly positively charged peptides (Hervé et al, 2008); peptides functionalized with TAT-like sequences (Muriel & Dowdy, 2006); peptides that bind LRP receptor family (Demeule et al, 2008); and antibodies against receptors that undergo receptor-mediated transcytosis, such as transferrin receptor antibody and insulin receptor antibody Pardridge et al, 1991; Jones & Shusta, 2007).

Pain is a major symptom of many different diseases. Research defines different types of pain on the basis of their neuronal and molecular mechanisms into nociceptive pain (resulting from inflammation and injury) and neuropathic pain (resulting from nerve disease or injury). Pain sensation (nociception) is evoked by potential or actual noxious stimuli or by tissue injury, and is mediated by a combination of peripheral and central (brain) mechanisms. Peripheral mechanisms of pain result from noxious stimuli that produce inflammation, which excites and sensitizes 'pain fibres'; the stimulus is transmitted through the spinal cord to the thalamocortical system in the brain where the pain sensation is given sensory discriminative aspect and affective aspect. The mediators of peripheral pain include inflammatory mediators such as prostaglandins, bradykinin, histamine, substance P, ATP, etc (Smith, 2008; Neiderberger et al, 2008). Drugs that prevent synthesis of inflammatory mediators (including non-steroidal and steroidal anti-inflammatory drugs) have analgesic effect.

In the CNS and the peripheral system, the key pain regulators are opioid receptors. There are 4 classes of opioid receptors: a) μ receptors; b) delta (δ) receptors; c) kappa (κ) receptors, and d) sigma (σ) receptors. These receptors are normally stimulated by endogenous peptides (endorphins, enkephalins and dynorphins) produced in response to noxious stimuli; endogenous enkephalins, for example, are relatively selective agonists of δ receptors. The opiod receptors can also be stimulated by drugs referred to as opioid analgesics, most of which are agonists of μ receptors (Trescot et al, 2008).

Pain management is accomplished through the use of analgesic drugs, which are the most used drugs of all classes. Three general classes of drugs are currently available for pain management: non-steriodal anti-inflammatories (NSAIDs), adjuvant analgesics, and opioids. NSAIDs act exclusively to reduce the inflammation and inflammatory mediators of pain (peripheral mechanisms) and are mainly used for mild to moderate pain indications. Adjuvant analgesics are used mainly for treatment of neuropathic pain and include various anti-depressants, anti-convulsants, neuroleptics, and corticosteroids. Centrally-acting plant opiates are the most frequently used analgesics for the relief of severe pain and include morphine and many derivatives (oxycodone, dihydrocodeine, hydrocodone, fentanyl, pentazocine, loperamide, fedotozine, naloxone, naltrexone, methyl nalozone, nalmefene, cypridime, beta funaltrexamine, naloxonazine, naltrindole, and nor-binaltorphimine). These drugs act through central pain mechanisms, where they have high selectivity for and various degree of potency on μ opioid receptors (Trescot et al, 2008).

Although opioid drugs can be very effective in pain management, they can cause several severe side effects, including:

respiratory depression that is proportional to their analgesia; this respiratory depression can be life-threatening. As a result, the range between the effective dose and a dose that produces respiratory depression is narrow. Because of this narrow therapeutic index, patients receiving opioid therapy must be closely monitored for signs of respiratory failure;

constipation in patients can be severe and may require prolonged hospitalization, or even surgical intervention;

development of physical dependence with repeated use is a characteristic feature of the opioid drugs, and the possibility of developing drug dependence is one of the major limitations of their clinical use;

cessation of opioid administration may result in a withdrawal syndrome. Symptoms of withdrawal are often the opposite of the effects achieved by the drug;

These unwanted effects can severely limit the use of opioid drugs, and are the consequence of the drugs' selectivity to μ opioid receptors.

There is therefore a need in the art for opioid analgesics that have a diminished likelihood of side effects, for example drugs that have selective activity on δ receptors. Enkephalins are endogenous opioid receptor agonists; they are potent and preferential δ opioid receptor agonists with weak agonist effect on μ receptors (Pencheva et al, 1999). Unfortunately, these neuropeptides do not cross the blood brain barrier (BBB), undergo rapid degradation by tissue peptidases (principally amino peptidase), and have very short half-lives in the blood stream (Polt et al, 2005; Weber et al, 1991).

Many other peptides that act through mechanisms independent from opioid receptors exist (e.g., neuropeptide Y, neurotensin). However, the analgesic activity of such peptides is only exhibited when administered centrally (i.e., intra-cerebroventricularly, intra-cerebrally); no activity is observed when administered peripherally (i.e., intravenously, subcutaneously), as they do not cross the blood-brain barrier.

Therefore, there is a need for a non-invasive brain-delivery technology for centrally-acting agents. There is a further need in the art for effective agents that may be administered non-invasively. Finally, there is a need in the art for agents with improved efficacy and superior side-effect profiles to relieve pain.

SUMMARY OF THE INVENTION

The present invention relates to compositions and methods for brain delivery of peptides. More specifically, the present invention relates to non-invasive brain delivery technology for centrally-acting analgesic peptides.

The present invention provides a compound comprising an antibody or fragment thereof capable of transmigrating across the blood brain barrier (BBB), and an analgesic peptide.

In the compound as described above, the antibody or fragment thereof may bind to TMEM30A. The analgesic peptide in the compound as described herein may act on opioid receptors, neuropeptide Y receptors, neurotensin receptors, galanin receptors, orexin receptors, somatostatin receptors, or any combination thereof.

The antibody or fragment thereof may comprise complementarity determining region (CDR) 1 sequence HYTMG (SEQ ID NO:1); a CDR2 sequence RITWGGDNTFYSNS-VKG (SEQ ID NO:2); and a CDR3 sequence GSTSTATPL-RVDY (SEQ ID NO:3). The antibody or fragment thereof in the above-described compound may also comprise the sequence:

```
                                           (SEQ ID NO: 4)
EVQLQASGGGLVQAGGSLRLSCAASGFKITHYTMGWFRQAPGKEREFV

SRITWGGDNTFYSNSVKGRFTISRDNAKNTVYLQMNSLKPEDTADYYC

AAGSTSTATPLRVDYWGKGTQVTVSS,
``` or a sequence substantially identical thereto. The antibody or fragment thereof may be a single domain antibody (sdAb).

The analgesic peptide may be an endogenous analgesic peptide, an exogenous analgesic peptide, or mutant or an analogue thereof. The analgesic peptide may be selected from the group consisting of opioid peptides, endorphins, enkephalins and dynorphins, galanin, neurotensin, neuropeptide Y, somatostatin, orexin A and B, conotoxin-derived peptides, analgesic peptides purified or derived from venoms of scorpion, cone shells, tarantula, or other species. In a specific example, the analgesic peptide may be selected from Dalargin, neuropeptide-Y or a fragment thereof, and neurotensin.

The present invention also provides a composition comprising the compound described above and a pharmaceutically acceptable diluent, carrier, or excipient.

Formulation(s) based on the presently described invention may be developed into clinically used analgesics for the treatment of pain, including, but not limited to pain associated with arthritis, particularly osteoarthritis and rheumatoid arthritis, post-operative pain, cancer-related pain, HIV-related pain, neuropathic pain syndromes, etc. The advantage of compounds of the present invention over other commercially available opioids is higher selectivity to delta class of opioid receptors in the brain, which renders them less likely to cause dependency.

The present invention also provides a method of treating pain comprising administering a compound comprising an antibody or fragment thereof capable of transmigrating across the blood brain barrier (BBB) and an analgesic peptide. The compound may be as described above. In the method as described, the pain may be associated with arthritis, post-operative pain, cancer-related pain, HIV-related pain, or neuropathic pain syndromes.

The present invention further provides a method of preventing or treating epileptic seizures comprising administering a compound or a composition as described herein, wherein the analgesic peptide also has anti-epiletogenic activity. In a non-limiting example, the analgesic peptide may be NPY or a fragment thereof, galanin, or cortistatin.

The Examples herein show that the conjugate of the hexapeptide leu-encephalin analog Dalargin with the blood-brain barrier-permeable single domain antibody FC5 is analgesic after systemic administration. It is further demonstrated that this conjugate has anti-nociceptive (analgesic) activity when injected both intra-cerebroventricularly and systemically. Similarly, the examples show that conjugation of a 36aa fragment of neuropeptide Y, which retains the neuropeptide Y receptor binding sites of the original 97 aa peptide, to FC5 also leads to analgesic activity after systemic administration. Analysis of nociception and analgesia was performed in mice using tail-flick test (model of acute pain) and in rats using paw-flick test (Hargreaves model of chronic pain). The data supports the usefulness of the blood-brain barrier-transmigrating sdAb FC5 in improving the systemic availability and efficacy of CNS-acting peptides.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein.

DETAILED DESCRIPTION OF THE INVENTION

Figure 1:
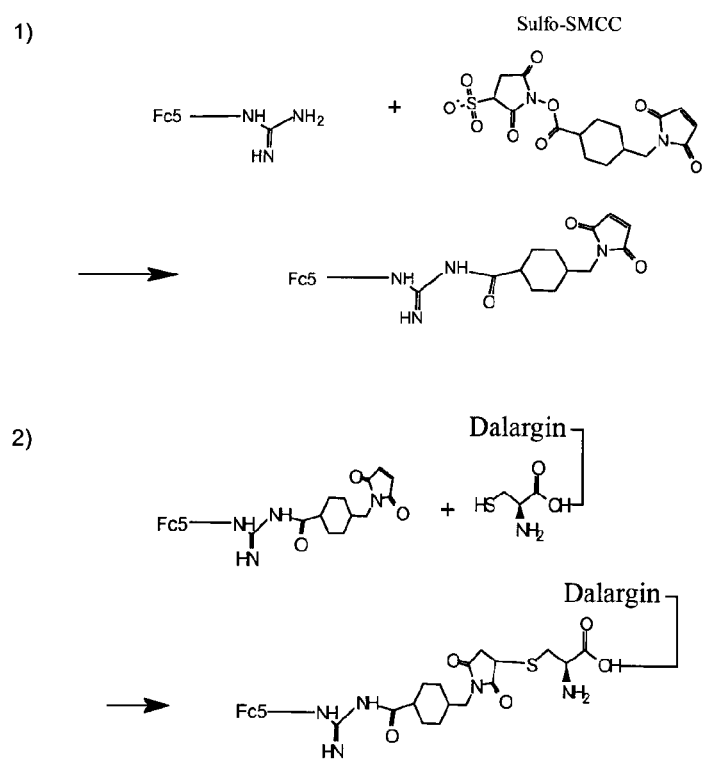
FIG. 1 shows the scheme for chemical synthesis of FC5-Dalargin. FC5 was first conjugated to the NHS group of Sulfo-SMCC cross-linker (1); then maleimide-activated FC5-sulfo-SMCC was conjugated to reduced Dalargin-cysteine (2).

The present invention relates to compositions and methods for brain delivery of analgesic drugs. More specifically, the present invention relates to non-invasive brain delivery technology for centrally-acting analgesic peptides.

The present invention provides a compound for central delivery of peptides comprising an antibody or fragment thereof capable of transmigrating across the blood brain barrier (BBB) and an analgesic peptide.

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the VH and VL domains. Chothia and Lesk (1987) define the "hypervariable loops" (H or L) based on the location of the structural loop regions in the VH and VL domains; the numbering for the hypervariable loops is defined as H1: 27-35; H2: 52-56; and H3: 95-102 (equivalent to CDR3 of Kabat numbering) for $V_H$/$V_H$H domains (Chothia and Lesk, 1997). As these individual schemes define CDR and hypervariable loop regions that are adjacent or overlapping, those of skill in the antibody art often utilize the terms "CDR" and "hypervariable loop" interchangeably, and they may be so used herein. The CDR amino acids in $V_H$ and $V_L$ regions are defined herein according to the Kabat numbering system (Kabat et al. 1991).

The region outside of the CDR is referred to as the framework region (FR). The FRs provide structural integrity to the variable domain and ensure retention of the immunoglobulin fold. This characteristic structure of antibodies provides a stable scaffold upon which substantial antigen-binding diversity can be explored by the immune system to obtain specificity for a broad array of antigens (Padlan et al, 1994).

An "antibody fragment" as referred to herein may include any suitable antigen-binding antibody fragment known in the art. The antibody fragment may be obtained by manipulation of a naturally-occurring antibody, or may be obtained using recombinant methods. For example, an antibody fragment may include, but is not limited to Fv, single-chain Fv (scFV; a molecule comprising $V_L$ and $V_H$ connected with a peptide linker), Fab, Fab', F(ab')$_2$, single domain antibody (sdAb), and multivalent presentations of these.

In a non-limiting example, the antibody fragment may be a single domain antibody (sdAb) derived from naturally-occurring sources. Heavy chain antibodies of camelid origin (Hamers-Casterman et al, 1993) lack light chains and thus their antigen binding sites consist of one domain, termed $V_H$H. sdAb have also been observed in shark and are termed $V_{NAR}$ (Nuttall et al, 2003); other sdAb may be engineered based on human heavy chain sequences (Jespers et al, 2004; To et al, 2005). As used herein, "sdAb" includes those directly isolated from $V_L$, $V_H$, $V_HH$ or $V_{NAR}$ reservoir of any origin through phage display or other display technologies and those generated through further modification of such sdAb by humanization, affinity maturation, stabilization, solubilisation (e.g., camelization), or other methods of antibody engineering. Also encompassed by the present invention are homologues, derivatives, or fragments that retain the antigen-binding function and specificity of the sdAb.

A person of skill in the art would be well-acquainted with the structure of a single-domain antibody (see, for example, 3DWT, 2P42 in Protein Data Bank). An sdAb comprises a single immunoglobulin domain that retains the immuglobulin fold; most notably, only three CDR form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb. The CDR of the sdAb are referred to herein as CDR1, CDR2, and CDR3, and are numbered based on Kabat numbering (Kabat et al. 1991).

By "capable of transmigrating across the BBB", it is meant that the antibody or fragment thereof crosses the blood-brain barrier; such antibodies or fragments may be used to carry other molecules, such as therapeutics, for delivery to the brain tissue. The antibody or fragment thereof may be any suitable antibody or fragment thereof known in the art to transmigrate the BBB.

In one example, the antibody or fragment thereof may bind to transmembrane protein 30A (TMEM30A), or isoforms, variants, portions, or fragments thereof. Without wishing to be limiting in any manner, TMEM30A may be an isoform or as shown in SEQ ID NOs: 11-13 or an extracellular fragments as shown in SEQ ID NO:14 (as described by WO 2007/036021), or sequences substantially identical thereto.

The antibody or fragment thereof may comprise a complementarity determining region (CDR) 1 sequence of HYTMG (SEQ ID NO:1); a CDR2 sequence of RITWGGDNTFYSNSVKG (SEQ ID NO:2); and a CDR3 sequence of GSTSTATPLRVDY (SEQ ID NO:3).

The terms "antibody" and "antibody fragment" ("fragment thereof") are as defined above. As previously stated, the antibody or fragment thereof may be a sdAb. The sdAb may be of camelid origin, and thus may be based on camelid framework regions; alternatively, the CDR may be grafted onto other antibody domains, for example but not limited to $V_{NAR}$ or human $V_H$ or $V_L$ framework regions. In yet another alternative, the CDR described above may be grafted onto the framework regions of other types of antibody fragments (Fv, scFv, Fab). The present embodiment further encompasses an antibody fragment that is "humanized" using any suitable method know in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the heavy chain CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, as is the affinity and specificity for its target (i.e., TMEM30A). CDR grafting is known in the art and is described in at least the following: U.S. Pat. No. 6,180,370, U.S. Pat. No. 5,693,761, U.S. Pat. No. 6,054,297, U.S. Pat. No. 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. No. 5,869,619, U.S. Pat. No. 5,766,886, U.S. Pat. No. 5,821,123, and European Patent No. 519596. Persons of skill in the art would be amply familiar with methods of preparing such humanized antibody fragments.

Without wishing to be limiting in any manner, the antibody or fragment thereof may comprise the FC5 sdAb described by Muruganandam et al, in WO 2002/057445. In a specific, non-limiting example, the antibody or fragment thereof may comprise the sequence

```
                                            (SEQ ID NO: 4)
EVQLQASGGGLVQAGGSLRLSCAASGFKITHYTMGWFRQAPGKEREFV

SRITWGGDNTFYSNSVKGRFTISRDNAKNTVYLQMNSLKPEDTADYYC

AAGSTSTATPLRVDYWGKGTQVTVSS,
``` or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; in a non-limiting example, the conservative amino acid mutation is a conservative amino acid substitution. A conservative amino acid substitution is defined herein as the substitution of an amino acid residue for another amino acid residue with similar chemical properties (e.g. size, charge, or polarity).

A conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "nonpolar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences ("substantially identical thereto") of the present invention may be at least 80% identical; in another example, the substantially identical sequences may be at least 80, 85, 90, 95, 96, 97, 98, 99, or 100% identical at the amino acid level to sequences described herein. Importantly, the substantially identical sequences retain the activity and specificity of the reference sequence. As would be known to one of skill in the art, certain amino acid residues within the framework regions of an antibody may be mutated (substituted or deleted) without affecting the functional properties of the antibody (antigen recognition and binding).

The compound of the present invention provides the antibody or fragment thereof linked to an analgesic peptide.

By the term "analgesic peptide", it is meant a protein sequence that exhibits an analgesic effect. The analgesic peptide may act on opioid receptors (such as µ receptors, delta (δ) receptors, kappa (κ) receptors, sigma (σ) receptors), neuropeptide Y receptors (such as Y1-Y6), neurotensin receptors (such as NTS1 and NTS2), galanin receptors (such as GalR1 and GalR2), orexin A and B receptors (such as OX1 and OX2), cortistatin receptors (such as SST1 to 5), or any combination thereof. The analgesic peptides may be endogenous peptides (such as endorphins, enkephalins and dynorphins, galanin, neurotensin, neuropeptide Y, somatostatin, orexin A and B), exogenous peptides (such as conotoxin-derived peptides, analgesic peptides purified from venoms of scorpion, cone shells (such as conotoxins, ziconotide), tarantula, or other species), or mutants or analogues thereof. In a non-specific, non-limiting example, the analgesic peptide may be selected from Dalargin, neuropeptide Y, and neurotensin.

By the term "linked", also referred to herein as "conjugated", it is meant that the antibody or fragment thereof is linked directly or indirectly (e.g., via a linker), covalently or non-covalently (e.g., adsorption, ionic interaction) to the analgesic peptide. A covalent linkage may be achieved through a chemical cross-linking reaction, through fusion using recombinant DNA methodology combined with any peptide expression system, such as bacteria, yeast or mammalian cell-based systems, or a combination thereof. Methods for linking the analgesic peptide to the antibody or fragment thereof would be well known to a person of skill in the art.

For example, and without wishing to be limiting in any manner, the present invention provides a compound comprising the FC5 sdAb linked to the enkephalin analogue Dalargin (Tyr-[D-Ala]-Gly-Phe-Leu-Arg; SEQ ID NO:5). The Dalargin peptide, which has D-Ala in second position in order to prevent enzymatic destruction, is used as a therapy for peripheral ulcers, and from this application it is known that Dalargin is stable in the blood stream (Weber et al, 1991). Independent of its anti-ulcer activity, Dalargin exhibits potent analgesic activity following intra-ventricular injection into the brain (Polt et al, 2005). However, it does not produce analgesia when given peripherally (Weber et al, 1991). From this it can be concluded that Dalargin, when administered into the blood stream, does not penetrate through the BBB in sufficient amounts to cause central nervous system (CNS) action. Dalargin has analgesic effect only after direct injection into the brain (Smith, 2008; Polt et al, 2005).

Another non-limiting example provides a compound comprising the FC5 sdAb linked to neuropeptide Y (NPY), which comprises the sequence:

(SEQ ID NO: 6)
MLGNKRLGLSGLTLALSLLVCLGALAEAYPSKPDNPGEDAPAEDMARYY

SALRHYINLITRQRYGKRSSPETLISDLLMRESTENVPRTRLEDPAMW, or to a fragment thereof. The fragment may be any fragment that is effective as an analgesic peptide, and that retains at least one of the neuropeptide Y receptor binding sites of the original peptide; for example, the fragment of NPY may comprise, but is not limited to YPSKPDNPGEDAPAED-MARYYSALRHYINLITRQRY (SEQ ID NO:7).

Neuropeptide Y (NPY) is the most abundant peptide in the human CNS, preferentially expressed in GABA-ergic interneurons and is a potent presynaptic inhibitor of glutamate-mediated synaptic actions. The peptide has various physiological functions mediated by several receptor types, Y1-Y6, which all belong to the G-protein coupled receptor superfamily. It is also important in cardiovascular physiology, feeding, anxiety and depression. NPY has analgesic effect through actions on Y1 receptors expressed in the dorsal horn, and anti-epileptogenic effect through action on Y2 receptors expressed in the hippocampus. NPYergic system may be a good target for the treatment of pharmaco-resistant forms of temporal lobe epilepsy, by acting on hyperexcitability, neuronal death or brain repair (Xapelli et al., 2006). In order to achieve new NPY-based analgesic and antiepileptic strategies, NPY needs to be able to reach its targets in the brain. This is currently possible only by direct intra-cerebroventricular injection of the peptide, because systemically injected peptide does not cross the blood-brain barrier (Woldbye, 1998).

Dalargin, or NPY or fragment thereof may be linked or conjugated to the FC5 via any method described above and known in the art. For example, and without wishing to be limiting in any manner, a cysteamide-OH residue may be placed at the N- or C-terminal of the peptide (using recombinant methods, during peptide synthesis, or by other methods) and the resulting peptide may be conjugated to the antibody or fragment thereof (which may be provided with a Sulfo-SMCC cross-linker) using chemistries known in the art, such as that shown in FIGS. 1 and/or 14.

The conjugation of the two molecules renders them pharmacologically effective after systemic injection, as shown in the present Examples. Specifically, both the Dalargin-FC5 and NPY-FC5 conjugates were shown to have analgesic effects after systemic administration, indicating their transmigration across the BBB and action on central receptors. The Dalargin-FC5 formulation acts on both δ and µ central opioid receptors, in contrast to other centrally-acting opioids that bind selectively µ receptors. Because of this mechanism of action, the Dalargin-FC5 formulation is less likely to cause addiction and other side effects mediated through µ receptors. NPY-FC5 acts on several types of receptors, of which Y1 are responsible for measured analgesic effect. In addition, and by virtue of NPY-FC5 being delivered to the brain after systemic injection, as demonstrated by analgesic effect, NPY-FC5 could have other beneficial therapeutic effects mediated via other receptors, most notably anti-epileptogenic effect through Y2 receptors.

The present invention also provides compositions or formulations comprising the compounds described herein. The compositions or formulations may further comprise pharmaceutically acceptable diluents, carriers, or excipients. By the term "pharmaceutically acceptable", it is meant that the diluent, carrier, or excipient is compatible with the compound of the present invention, and is not deleterious to the recipient of the composition. The diluent, carrier, or excipient may be any suitable diluent, carrier, or excipient known in the art, and may vary based on the route of administration and dosage required.

The compounds and formulations of the presently described invention may be developed into clinically used analgesics for the treatment of pain, including, but not limited to pain associated with arthritis, particularly osteoarthritis and rheumatoid arthritis, post-operative pain, cancer-related pain, HIV-related pain, neuropathic pain syndromes, etc. The advantage of compounds of the present invention over other commercially available opioids is their decreased likeliness to cause dependency.

The present invention further provides a method of treating pain comprising administering a compound or a composition as described herein. The method as described may be used for the treatment of pain, including, but not limited to pain associated with arthritis, particularly osteoarthritis and rheumatoid arthritis, post-operative pain, cancer-related pain, HIV-related pain, neuropathic pain syndromes, or other types of pain.

The present invention will be further illustrated in the following examples. However, it is to be understood that these examples are for illustrative purposes only and should not be used to limit the scope of the present invention in any manner.

Example 1

FC5 sdAb Cloning, Expression and Purification

FC5 single domain antibody (sdAb) was cloned, expressed and purified in preparation for conjugation to analgesic peptides. FC5 was expressed in fusion with His5 and c-myc tags) to allow for purification by immobilized metal affinity chromatography using HiTrap Chelating™ column and for detection by immunochemistry, respectively.

Briefly, DNA encoding sdAb FC5 (SEQ ID NO:12) was cloned into the BbsI/BamHI sites of plasmid pSJF2 to generate expression vector for FC5 (Muruganandam et al, 2002). The DNA constructs were confirmed by nucleotide sequencing on 373A DNA Sequencer Stretch (PE Applied Biosystems) using primers fdTGIII, 5'-GTGAAAAAATTATTAT-TATTCGCAATTCCT-3' (SEQ ID NO:8) and 96GIII, 5'-CCCTCATAGTTAGCGTAACG-3' (SEQ ID NO:9).

Single clones of recombinant antibody-expressing bacteria E. coli strain TG1 were used to inoculate 100 ml of M9 medium containing 100 µg/ml of ampicillin, and the culture was shaken overnight at 200 rpm at 37° C. The grown cells (25 ml) were transferred into 1 L of M9 medium (0.2% glucose, 0.6% $Na_2HPO_4$, 0.3% $KH_2PO_4$, 0.1% $NH_4Cl$, 0.05% NaCl, 1 mM $MgCl_2$, 0.1 mM $CaCl_2$) supplemented with 5 µg/ml of vitamin B1, 0.4% casamino acid, and 100 µg/ml of ampicillin. The cell culture was shaken at room temperature for 24 hours at 200 rpm and subsequently supplemented with 100 ml of 10× induction medium Terrific Broth containing 12% Tryptone, 24% yeast extract, and 4% glycerol. Protein expression was induced by adding isopropyl-µ-D-thiogalactopyranoside (IPTG; 1 mM). After induction, the culture was shaken for an additional 72 hours at 25° C., and the periplasmic fraction was extracted by the osmotic shock method.

The FC5 sdAb was purified by immobilized metal-affinity chromatography using HiTrap Chelating™ column (Amersham Pharmacia Biotech; Piscataway, N.J.). Bound FC5 was eluted in 10 mM HEPES buffer, 500 mM NaCl, pH 7.0, with a 10-500 mM imidazole gradient and peak fractions were extensively dialyzed against 10 mM HEPES buffer, 150 mM NaCl, 3.4 mM EDTA, pH 7.4.

Example 2

FC5-Dalargin Conjugation

The FC5 sdAb prepared in Example 1 was conjugated to Dalargin, as described below.

4 mg of dialyzed FC5 from Example 1 was placed in a 1.5-ml micro-centrifuge tube. Sulfo-SMCC was added to the FC5 in a 10× molar ratio; specifically, 232 µl of 5 mg/ml Sulfo-SMCC was added. The micro-centrifuge tube containing the mixture was then flushed with nitrogen gas and incubated for 2 hours at room temperature (RT). Once the reaction is done, the unreacted Sulfo-SMCC was removed from the maleimide-activated FC5 using Millipore Amicon Ultra-4, Ultracel 3K column. The solution was added to the column, the volume was completed to 4 ml with PBS, and the mixture was spun at 4000×g for 13 minutes at 10° C. This process was repeated once more, and the product was washed 3 times.

Separately, and during the above steps, Dalargin-cysteamide-OH (Dalarin-cys) was reduced with TCEP. A 5 mg/ml stock of Dalargin-cys dissolved in PBS was prepared and flushed with $N_2$. Similarly, a 100 mM TCEP solution in $N_2$ flushed milli-Q $H_2O$. Then, 58 µl of the 100 mM TCEP was added to 261.5 µl of 5 mg/mi Dalargin-cys and 11 µl of 0.5M EDTA. The mixture was then flushed with nitrogen, sealed and incubated at RT for 30 minutes.

The purified maleimide-activated FC5 was mixed with the reduced Dalargin-cys, flushed with nitrogen, sealed and incubated at RT for 90 minutes and then overnight at 4° C. The next day, the unreacted Dalargin and the TCEP were removed using Millipore Amicon Ultra-4, Ultracel 3K column. The solution was added to the column, the volume was completed to 4 ml with PBS, and the mixture was spun at 4000×g for 13 minutes at 10° C. This process was repeated once more, and the product was washed 3 times.

Figure 2:
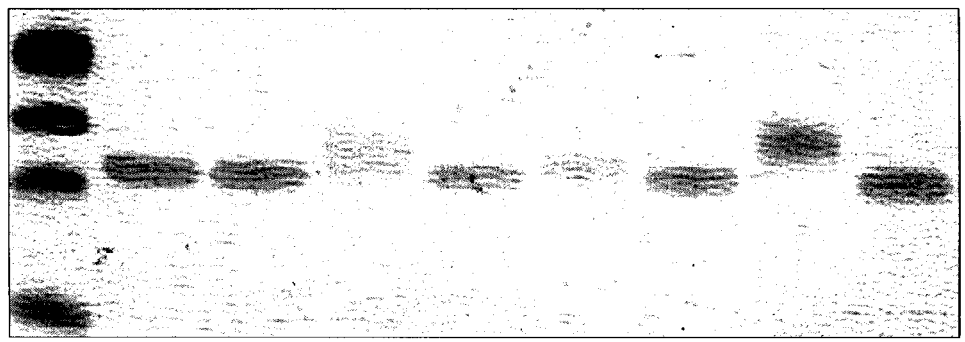
FIG. 2 is a photograph of a 16% tricine gel electrophoresis of various component and by-products of the reactions described in FIG. 1. Lane 1—2 μg FC5; Lane 2—2 μg FC5; Lane 3—2 μg FC5-SMCC-Dalargin (FC5-Dal); Lane 4—2 μg FC5; Lane 5—2 μg FC5-SMCC; Lane 6—2 μg FC5; Lane 7—2 μg FC5-Cy5.5; Lane 8—2 μg FC5. FC5 alone has molecular weight of 14 kD; FC5-Dalargin showed molecular weight of 15 kDa. FC5 conjugate with Cy5.5 (1 kD) was used as a control (MW FC5-Cy5.5=15 kD)

The samples were then run on a 16% tricine gel (at 125 Volts for 2.5 hr at 4° C.) to confirm shift in molecular weight size after conjugation. FIG. 2 is a photograph of the 16% tricine gel electrophoresis of various component and by-products of the reactions. Successful conjugation of FC5 sdAb to Dalargin-cysteamide (~1 kD) is shown. FC5 alone has molecular weight of 14 kD; FC5-Dalargin showed molecular weight of 15 kDa. FC5 conjugate with Cy5.5 (1 kD) was used as a control (MW FC5-Cy5.5=15 kD).

Example 3

Transport of the FC5-Dalargin Across In Vitro Blood Brain Barrier Model

To show that the FC5-Dalargin conjugate (Example 2) maintains the blood-brain barrier permeability of FC5, an in vitro assay was used as described below.

FC5 and FC5-Dalargin were labelled by covalent conjugation to Cy5.5 N-hydroxysuccinimide (NHS) ester using methods recommended by the manufacturer (GE Healthcare). Cy5.5 NHS was bound to FC5 through a thioether covalent bond.

Immortalized Adult Rat brain endothelial cells (ARBEC) were used as the in vitro blood brain barrier model. ARBEC (80,000 cells/membrane) were seeded on a 0.5% gelatine-coated Falcon tissue culture inserts (pore size-1 µm; surface area 0.83 cm$^2$) in 1 ml of growth medium. The bottom chamber of the insert assembly contained 2 ml of growth medium supplemented with the fetal human astrocyte-conditioned medium in a 1:1 (v/v) ratio.

Transport studies were performed 7 days post-seeding. Filter inserts were rinsed with transport buffer (PBS containing 5 mM glucose, 5 mM $MgCl_2$, 10 mM HEPES, 0.05% BSA, pH 7.4) and allowed to equilibrate at 37° C. for 30 minutes. Experiments were initiated by adding 10 µg/ml Cy5.5-labelled FC5-Dalargin or Cy5.5-labelled FC5 to the apical chamber. Aliquots (100 µl) were collected from the opposite chamber at various time intervals (5, 15, 30, 60, 120 minutes) and replaced with fresh buffer. The amount of FC5-Dalargin transported across HCEC monolayers was determined by fluorescence in a fluorescence plate reader. To control for ARBEC membrane integrity and to estimate paracellular diffusion, the apical-to-basolateral and basolateral-to-apical clearance rates of [$^{14}$C]-sucrose was determined and calculated essentially as previously described (Muruganandam et al, 2002; Garberg et al, 2005) across the same monolayers used for FC5-Dalargin transport studies. Sample-associated radioactivity was measured using a Mircobeta Trilux liquid scintillation counter (Wallac, Finland). Sucrose permeability Pe (0-30 min) was calculated to be $0.829 \times 10^{-3}$ cm/min indicative of an integral cell monolayer.

Figure 3:
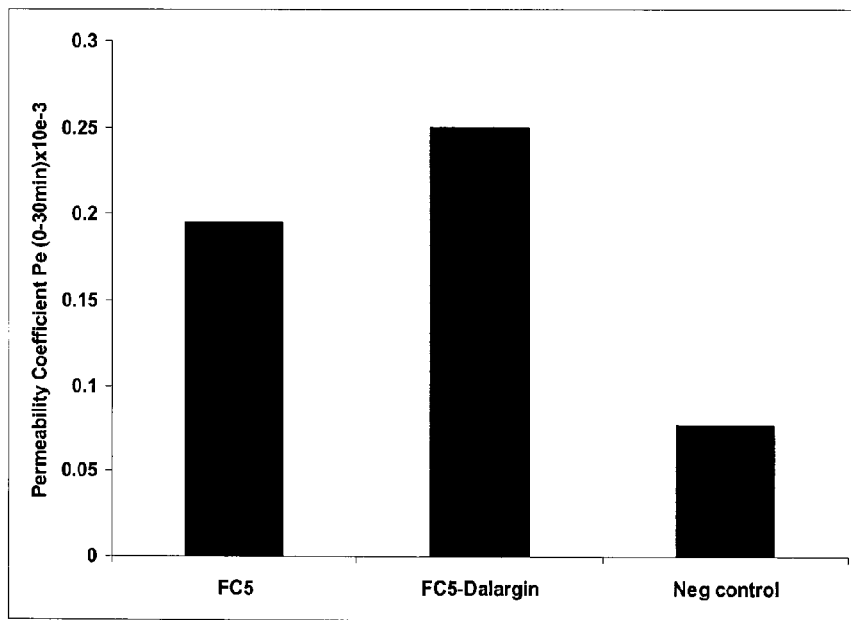
FIG. 3 is a bar graph summarizing the results of transmigration of FC5 and FC5-Dalargin across in vitro model of the blood-brain barrier composed of immortalized rat brain endothelial cells and immortalized rat astrocyte-conditioned media.

Results are summarized in FIG. 3. FC5-Dalargin transmigrated across the blood-brain barrier composed of immortalized rat brain endothelial cells in this model to a level similar to FC5 alone. The results indicate that FC5-Dalargin conjugate retained the ability to cross the BBB (function of FC5). Permeability co-efficients (Pe) were as follows: FC5=$0.195 \times 10^{-3}$ cm/min; and FC5-Dalargin=$0.250 \times 10^{-3}$ cm/min. A negative control single domain antibody with a molecular weight of 13 kDa equal to molecular weight of FC5 was used for comparison and gave a Pe of $0.077 \times 10^{-3}$ cm/min.

Example 4

Opioid Receptor-Binding Studies

To demonstrate that the FC5-Dalargin conjugate of Example 2 maintains opioid receptor binding activity, displacement studies were done against radiolabelled $^3$H-DAMGO, a µ receptor agonist, in isolated rat brain membranes.

FC5 antibody binds to brain capillaries, therefore to exclude the binding of FC5 in the Dalargin-FC5 formulation, capillary depletion was initially performed. Briefly, adult rat brain cortices were homogenized by hand in buffer A (103 mM NaCl, 4.7 mM KCl, 2.5 mM $CaCl_2$, 1.2 mM $KH_2PO_4$, 1.2 mM $MgSO_4$, 15 mM HEPES) in a 1/3.5 (w/v) dilution (this volume is referred to as 1 Volume). An equal volume of 30% dextran was then added to yield a final concentration of 15% dextran. The homogenate was centrifuged at 5800×g (10,000 rpm; Beckman L8-70 Ultracentrifuge, Rotor: SW 40) for 20 min at 4 degrees. The upper parenchyma layer was then collected and centrifuged under the same conditions. The upper parenchyma layer was again collected, and 1 Volume of 50 mM Tris-buffer pH 7.4 containing [2×] of protease inhibitor was added to the collected parenchyma. The mixture was homogenized using a motorized pestle. The homogenate was centrifuged at 46,000×g for 15 minutes at 4° C. The supernatant was removed and the pellet re-suspended in 1 Volume Tris-buffer pH 7.4 containing [2×] of protease inhibitor. The re-suspended pellet was incubated at 37° C. for 15 minutes with agitation in a 50 ml conical tube to dissociate endogenous opioids from receptors. After incubation, the homogenate was centrifuged at 46,000×g for 15 minutes at 4° C. The supernatant was again removed and the pellet re-suspended in 1 to 1.5 Volume Tris-buffer pH 7.4 containing [1×] of protease inhibitor. The membrane preparation was aliquoted into 1.5 ml tubes in 1 ml samples and stored at −80° C.

Opioid Receptor binding assay used a µ opioid receptor agonist, $^3$H-DAMGO, to bind to opioid receptors present in the rat brain membrane preparation. Displacement studies were done with unlabelled ligands, Dalargin, and Dalargin-FC5. Briefly, diluted reagents were prepared using 50 mM Tris-buffer pH7.4, as follows:

i. 1 µM $^3$H-DAMGO: 0.25 µl 20 mM $^3$H-DAMGO and 5 ml Tris-buffer;

ii. 500 nM Dalargin: 3.62 µl 1.38 mM Dalargin and 10 ml Tris-buffer;

iii. 500 nM Dalargin-cys: 3.94 µl 1.27 mM Dalargin-cys and 10 ml Tris-buffer;

iv. 500 nM FC5-Dal: 16.67 µl 30 µM FC5-Dal and 1 ml Tris-buffer;

v. 500 nM FC5: 2.73 µl 183 µM FC5 and 1 ml Tris-buffer.

200 µl of membrane preparation (7.15 mg/ml; diluted 1:3 in Tris buffer) was added to each well of a 96-well plate. Tris-buffer was added to each well, followed by a range of Dalargin concentrations, followed by $^3$H-DAMGO. The reaction mixture was left at RT with gentle orbital shaking for 1.5 hr. A scintillation cocktail was then added and radioactive counts were measured using beta scintillation counter.

To calculate $IC_{50}$ and $K_i$ value for Dalargin formulas, DPM values were first converted to molar units using the equation: Molar concentration of labelled ligand [L]=(specific counts)* (1/2200000)*(1/specific activity)*1000. Specific activity for $^3$H-DAMGO was 56.8 Ci/mmol. Percentage specific bound at each concentration of unlabelled competitor was calculated using the formula: % specific bound=Bound/Total bound*100. $K_i$ values are calculated from the obtained IC50 values by the Cheng and Prusoff equation: $K_i$=IC50/(1+L/$K_d$), where L and $K_d$ are the concentration and affinity of the radiolabelled ligand $^3$H-DAMGO. The $IC_{50}$ value was calculated by GraphPad Prism. $K_i$ value is the inhibition constant for the opioid (i.e, the concentration of competing ligand in a competition assay which would occupy 50% of the receptors if no radioligand were present).

Figure 4:
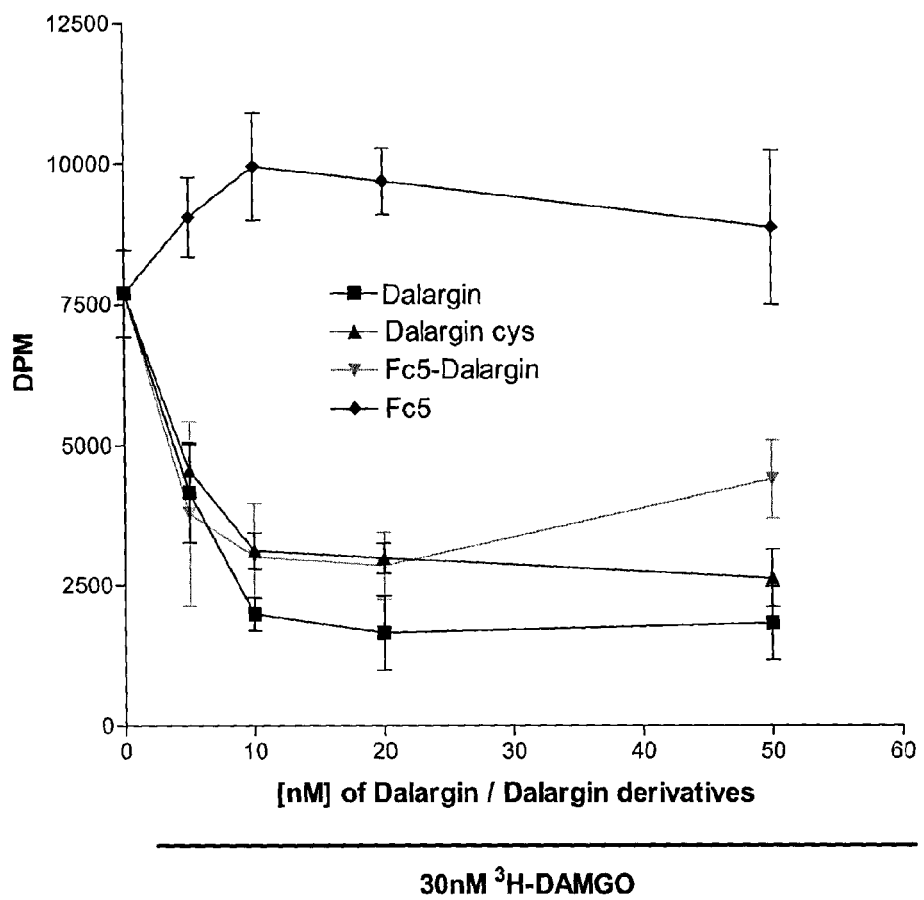
FIG. 4 shows the results of receptor binding competition assays of Dalargin and Dalargin derivatives (Dalargin-cys and Dalargin-FC5) against 30 nM $^3$H-DAMGO in isolated rat brain membranes.

Results of receptor binding competition assays are shown in FIG. 4. FC5 antibody alone did not displace $^3$H-DAMGO. However, FC5-Dalargin demonstrated similar displacement potency to Dalargin-cys, and both were only slightly less potent than Dalargin, suggesting that FC5-Dalargin conjugate retains opioid receptor-binding activity.

Example 5

Analgesic Activity of FC5-Dalargin in Acute Pain (Tail Flick Assay)

The Tail Flick assay was used to measure the analgesic activity of the FC5-Dalargin conjugate of Example 2. This assay is a pain receptive assay in which a mouse is placed within a restraining tube with its tail protruding. The tail is placed on a level surface, a radiant heat is applied to the tail and the latency of the mouse to remove its tail from the heat is recorded. This latency is used as a measure to indicate analgesic activity of injected compounds—analgesia is demonstrated by an increase in time to occurrence of a tail flick response. All procedures using animals were approved by the institutional animal care committee and complied with the guidelines established by the Canadian Council on Animal Care.

Male CD-1 mice (23-25 g) were obtained from Charles River and bred locally; 6-8 week old mice were used in the assay. The IITC Model 336 Plantar/Tail Analgesic Meter with True tail Temp and Heated Glass was used for the tail flick assay. In order to acclimatize the mice to the machine, each mouse was briefly placed in the restraining tube 2-3 times before the test occurred. Intensity of the lamp was adjusted to produce a latency time of 3-4 sec. The cut-off latency time (a time when the experiment is terminated) was set at 10 sec. Baseline values for tail flick latency time were determined before drug administration in each animal. Basal tail flick latency time was 3±1 seconds.

Immediately after setting/testing baseline latency time, animals were lightly anaesthetized with isoflurane and received either intra-cerebroventricular injection or intra-carotid injection of FC5-Dalargin, FC5, or Dalargin.

For intra-cerebroventricular injections, a longitudinal incision was made in the scalp to identify the bregma; then animals received a unilateral 5 µl intra-cerebroventricular injection of either FC5-Dalargin or Dalargin alone approximately 2 mm caudal and 1 mm lateral with respect to the bregma, and 3 mm ventral from the skull surface. Injections were made using a Hamilton syringe equipped with a 25-gauge needle. Injection depth was controlled by a plug on the needle to prevent more than 2 mm penetration beyond the skull surface.

For intra-carotid injections, anesthesia was induced with 4% isoflurane and maintained with 2.7% isoflurane in 69% $N_2O$ and 30% $O_2$ using a vaporizer. The left common carotid artery (CCA) was exposed and a catheter made from PE10 tubing was introduced and secured in place. A temporary ligature was placed on the left external carotid artery (ECA). In one experiment, an equimolar dose of 30 nmole of FC5-Dalargin or Dalargin alone (approx 0.86 mg/kg of Dalargin in each composition) was injected into the internal carotid artery via the CCA. In another experiment, an equimolar dose of 62 nmole of FC5-Dalargin or Dalargin alone (approximately 1.72 mg/kg of Dalargin) was also injected into the internal carotid artery via the CCA. The catheter was then removed and the CCA was permanently tied off; the ligature of the ECA was removed. A small amount of 2% xylocaine gel was applied to the inner surface of the wound, which was sutured closed.

Following the intra-carotid injections or intra-cerebroventricular injections, the animals were tested for tail flick latencies at 5, 10, 15, 30, 45 and 90 minutes post-injection. The nociceptive sensitivity was determined by converting the recorded analgesic tail-flick times to a percent maximal possible effect (% MPE):

% MPE=[(recorded flick time−baseline)/(maximum time(10 s)−baseline)]×100

Figure 5:
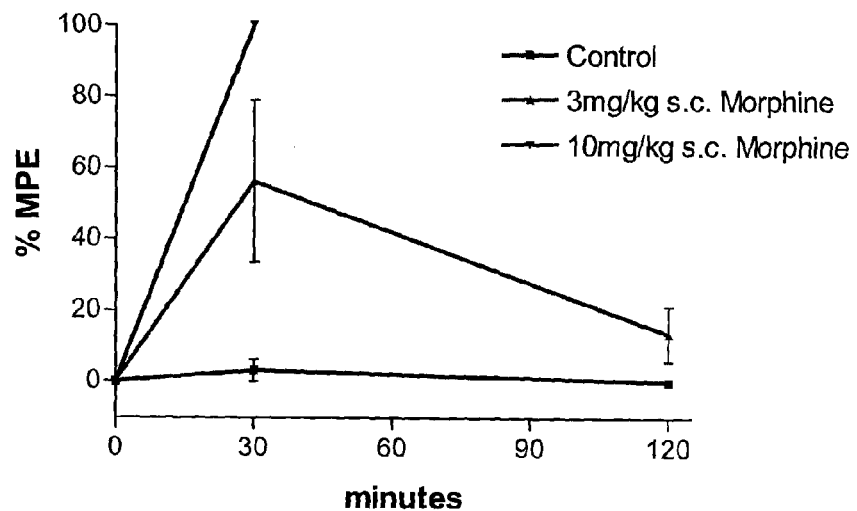
FIG. 5 shows the latency time in tail-flick assay induced by escalating doses of morphine—determination of maximal analgesic effect. The morphine dose response was determined by injecting 3 mg/kg or 10 mg/kg of morphine subcutaneously and determining the latency of tail flick at different time points. The maximal response −10 sec latency (cut-off time) was induced by 10 mg/kg morphine 30 min after s.c. injection.

The analgesic effect of FC5-Dalargin injected intra-cerebroventricularly (FIG. 6) or systemically at two doses, 0.86 mg/kg (FIG. 7) and 1.72 mg/kg (FIG. 8), was compared ('benchmarked') against the maximal effect of morphine at two doses (3 mg/kg, and 10 mg/kg) injected subcutaneously (FIG. 5). All animals injected with the 10 mg/kg of morphine showed maximally allowed latency of 10 sec, 30 min after injection. 3 mg/kg of morphine (s.c) produced approximately 50% of the maximal analgesic effect (observed with 10 mg/kg morphine) (FIG. 5).

Figure 6:
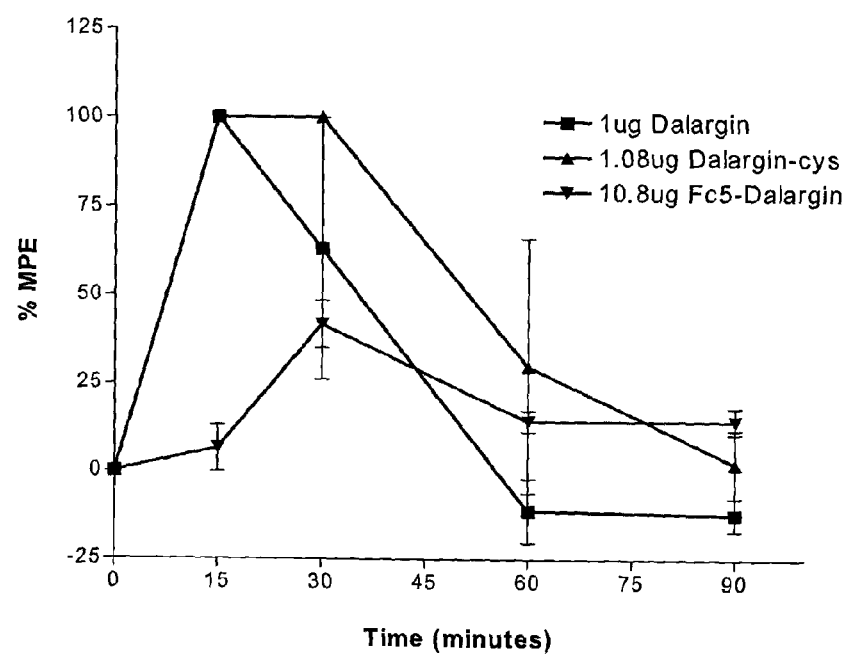
FIG. 6 shows a summary of the analgesic effects of Dalargin, Dalargin-cys and Dalargin-FC5 administered intra-cerebroventricularly measured by the tail-flick assay.

FIG. 6 shows the analgesic activity of Dalargin and Dalargin-FC5 administered intra-cerebroventricularly as described above. Dalargin and Dalargin-cys showed a similar analgesic effect reaching maximal latency of response, essentially comparable to that induced by 10 mg/kg morphine (FIG. 5), 15-min and 30-min after injection and returning to basal levels 60 min after injection. FC5-Dalargin induced maximal analgesia 30 min after injection that reached 40% of maximum effect and which persisted at 10-15% above basal levels for up to 90 min. Optimization of the dosage may result in greater % of maximum effect.

Figure 7:
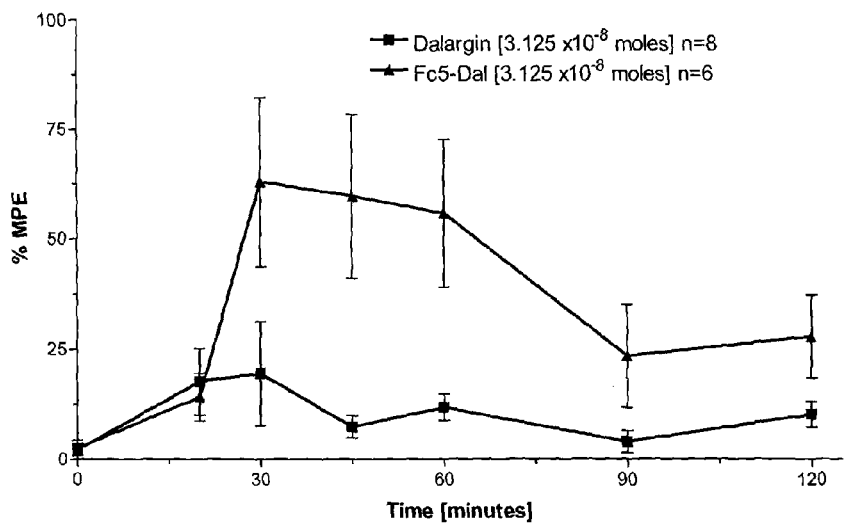
FIG. 7 shows the analgesic activity of Dalargin and FC5-Dalargin (dosage: 0.86 mg/kg Dalargin) after intra-carotid (systemic) injection in the tail-flick pain model in mice.
Figure 8:
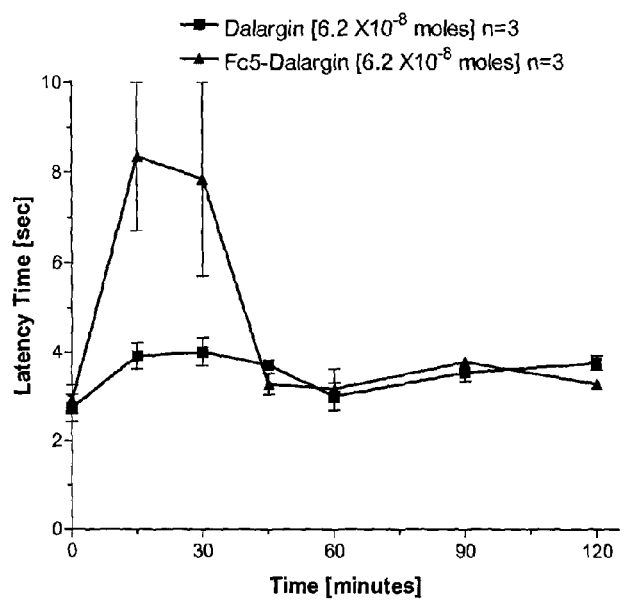
FIG. 8 shows the analgesic activity of Dalargin and FC5-Dalargin (1.72 mg/kg of Dalargin) after intra-carotid (systemic) injection in the tail-flick pain model in mice.

Results for the analgesic activity of Dalargin and FC5-Dalargin after intra-carotid injection at 0.86 mg/kg and 1.72 mg/kg are shown in FIG. 7 and FIG. 8, respectively. Table 1 gives a comparison of % MPE among two subcutaneous doses of morphine (see Example 6), two intra-carotid does of Dalargin, and two intra-carotid doses of Dalargin-FC5 at 30 min following injection

TABLE 1

Comparison of % MPE for morphine, Dalargin and FC5-Dalargin.

| Treatment | % MPE (30 min) |
|---|---|
| Morphine (10 mg/kg sc) | 100% |
| Morphine (3 mg/kg sc) | 56% |
| Dalargin (0.86 mg/kg ic) | 19% |
| Dalargin (1.72 mg/kg ic) | 17% |
| FC5-Dal (0.86 mg/kg ic) | 63% |
| FC5-Dal (1.72 mg/kg ic) | 66% |

No analgesic effect was observed after the intra-carotid injection of Dalargin; this is consistent with previous observations that Dalargin does not cross the BBB and has no analgesic effects after systemic administration. After intra-carotid injection of FC5-Dalargin, increased latency times reaching 63% and 66% of a maximal latency induced by 10 mg/kg morphine were observed 30 minutes after administration of the conjugate.

Example 6

Analgesic Activity of FC5-Dalargin in Chronic Pain (Paw Flick Assay)

The Paw Flick test, also known as the Hargreaves Method, was used to measure the analgesic activity of the FC5-Dalargin conjugate of Example 2 in chronic pain.

Chronic inflammatory pain was induced in 4-6 week old male Wistar rats, by a intra-plantar (i.pl.) injection (100 µl with a 30-gauge needle) of complete Freund's adjuvant in sterile water in a ratio of 1:1 in the right hind paw under brief isoflurane anesthesia (3%). Three days after CFA injection the putative antinociceptive effect of different compounds was quantified by measuring latencies of withdrawal of both hind limb paws (ipsilateral and contralateral to CFA injection) in response to radiant heat using digitalized plantar Analgesia Meter for paw stimulation (IITC Model #336TG Life Science, Inc.). A rapid paw withdrawal on the side of CFA injection (compared to the contralateral non-injected paw) was indicative of inflammatory pain. During the training period (before experiments), the light-intensity lamp was adjusted to elicit baseline paw withdrawal latencies between 17 to 20 s (in rats). If a withdrawal response does not occur within 20 s, the light beam was automatically turned off and the animal was assigned the maximum score. Results were analyzed as temporal courses of paw withdrawal latency (sec) versus time (min or hrs) and expressed as % of maximum possible effect (% MPE) as described in Example 5. A subcutaneous injection of morphine 10 mg/kg served as a positive control.

Intra-Cerebroventricular Injection:

For intra-cerebroventricular injections in rats, a longitudinal incision was made in the scalp to identify the bregma; then animals received a unilateral 5 µl intra-cerebroventricular injection of either FC5-Dalargin or Dalargin alone approximately 0.8 mm anterioposterior (AP) level of bregma, 1.5 mm with respect to the midline and 3.5 mm ventral from the skull surface. Injections were made using a Hamilton syringe equipped with a 25-gauge needle. Injection depth was controlled by a plug on the needle to prevent more than 3.5 mm penetration beyond the skull surface.

Figure 9:
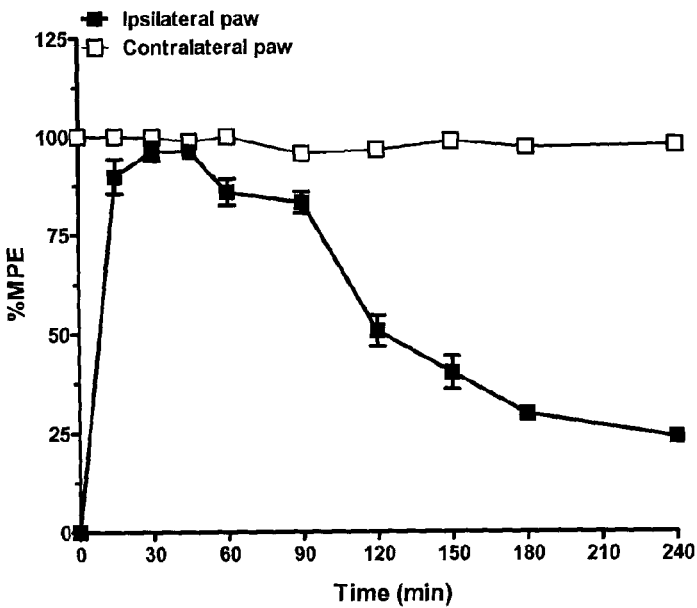
FIG. 9 shows the analgesic effect of 10 mg/kg morphine (administered subcutaneously) in the paw flick assay (chronic pain model).

Subcutaneous injection of morphine at 10 mg/kg (control) resulted in prompt increase in CFA-injected paw withdrawal latency to values of the contralateral, non-inflamed paw lasting for 60 min and slowly diminishing over subsequent 3 hours (FIG. 9).

Figure 10:
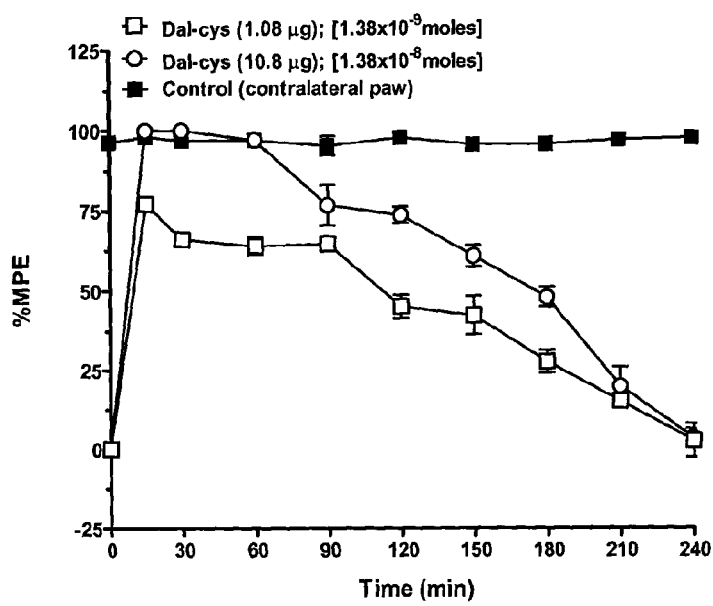
FIG. 10 shows the analgesic effects of Dalargin-cys at two different doses (1.08 μg and 10.8 μg) after intra-cerebroventricular injection in paw flick assay (chronic pain model).
Figure 11:
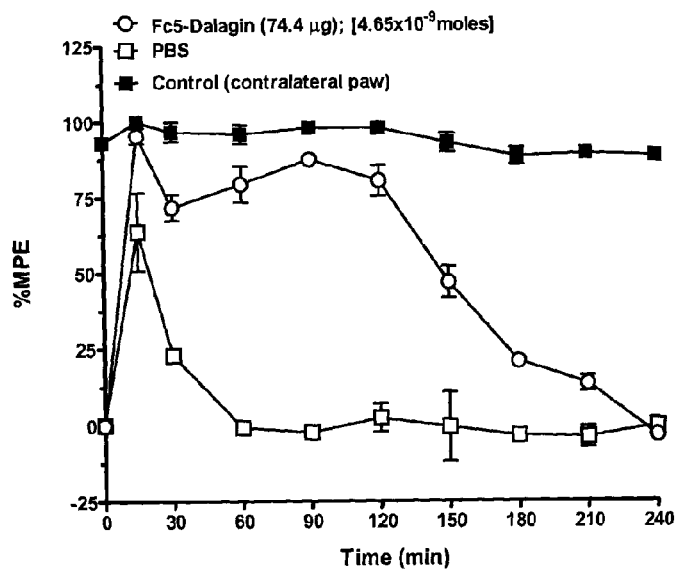
FIG. 11 shows the analgesic effects FC5-Dalargin (74.4 μg) after intra-cerebroventricular injection in the paw flick assay (chronic pain model).

Intra-cerebroventricular (icy) injection of Dalargin-cys (FIG. 10) at 2 doses showed a significant analgesic effect, i.e., increase latency of inflamed paw withdrawal; a lower dose of 1.08 µg achieved 75% of maximal effect, whereas a 10.08 µg dose resulted in 100% MPE, with a profile similar to that obtained with morphine (FIG. 9). Similarly, icy injection of FC5-Dalargin (74.4 µg—corresponding to the higher dose of Dalargin-cys from FIG. 10) resulted in complete analgesia sustained over 120 min (FIG. 11). IPBS injection served as control in these experiments (FIG. 11, open squares) to control for 'wash-out' of analgesic used during surgical procedure of icy injections. As shown in FIG. 11, the analgesic effect of anaesthesia received during the injection procedure disappears 30 min after the procedure; hence, analgesic effect observed with FC5-Dalargin lasting over 120 min is caused by intrinsic activity of Dalargin on opioid receptors and not by anaesthesia received during injection procedures.

Figure 12:
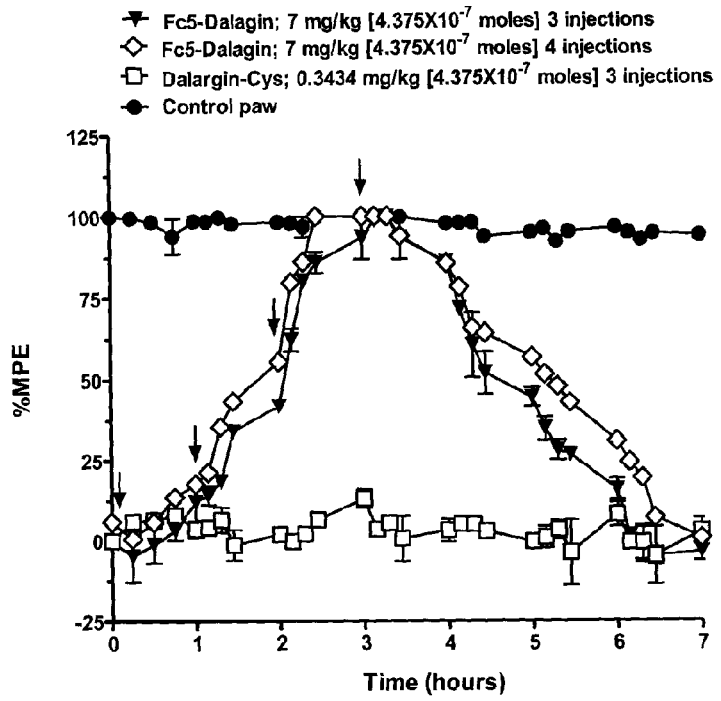
FIG. 12 shows the analgesic effects of FC5-Dalargin after intravenous injection. The maximal analgesic effect of FC5-Dalargin was reached after 3 injections; a lack of analgesic effect for Dalargin-cys (administered intravenously) in 3 injections was observed.
Figure 13:
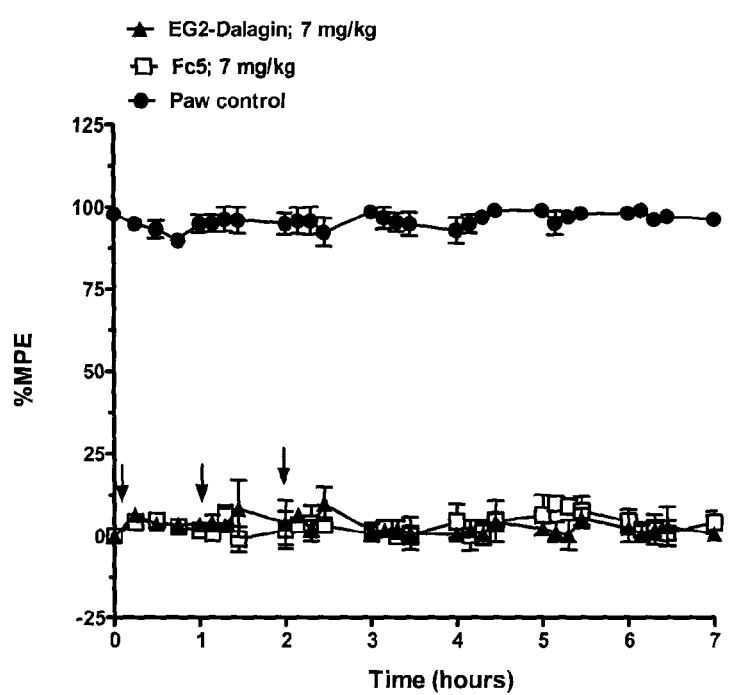
FIG. 13 shows a lack of analgesic effects of the EG2-Dalargin conjugate and of FC5 after intravenous injections (3 injections).

Intravenous Injection:

FC5-Dalargin was then injected intravenously (in the tail vein; 7 mg/kg) and its analgesic effect was compared to Dalargin-cys (0.34 mg/kg; reflecting the Dalargin dose in FC5-Dalargin construct), to FC5 (7 mg/kg) and to the construct of Dalargin with a control anti-EGFR single domain antibody, EG2, that does not cross the blood brain barrier (EG2-Dalargin; 7 mg/kg). Given the short systemic half life of Dalargin, FC5, and FC5- and EG2-Dalargin formulations, three i.v. injections of each compound were delivered at 0, 1, and 2 hours, and the analgesic effect was monitored in paw flick assay every 15-min over a 7-hour period. Dalargin-cys did not increase latency of withdrawal of the inflamed paw at any time during and after three i.v. dosing (FIG. 12, open squares). In contrast, FC5-Dalargin induced cumulative analgesia after each i.v. dosing, reaching 100% MPE 45 min-1 hour after the third injection and gradually 'washing-out' over a subsequent three hours (FIG. 12, closed triangles), similar to what was observed after intra-cerebroventricular injections of Dalargin-cys and FC5-Dalargin (FIGS. 10 and 11). If Fc5-Dalargin injection was given $4^{th}$ time at 3 h (FIG. 12, open polygons), the 'wash-out' (i.e., disappearance of analgesic effect) was somewhat extended. Neither FC5 alone nor EG2-Dalargin construct induced any analgesic effect when administered in the same manner (i.e., 3 injections at 0, 1, and 2 h) (FIG. 13). These date demonstrate that, while Dalargin is potent analgesic when administered centrally, it is ineffective when administered peripherally because it does not cross the blood-brain barrier. When Dalargin is functionalized with the blood-brain barrier 'carrier' single domain antibody, FC5, Dalargin becomes efficacious in inducing analgesia in chronic pain because FC5 enables its delivery across the blood brain barrier to the sites of its pharmacological action, central opioid receptors.

As humans express the same types of analgesia-inducing receptors, in this case opioid receptors, as rodents, the FC5-Dalargin construct would be capable of transmigrating the BBB in humans and acting centrally on the opioid receptors of the human brain. Therefore, FC5-Dalargin conjugate can be used as peripherally-active analgesic for acute or chronic pain indications with improved side-effect profile compared to morphine and other opioid analgesics.

Example 7

Conjugation of FC5 with the Analgesic Peptide Neuropeptide Y (NPY)

Figure 14:
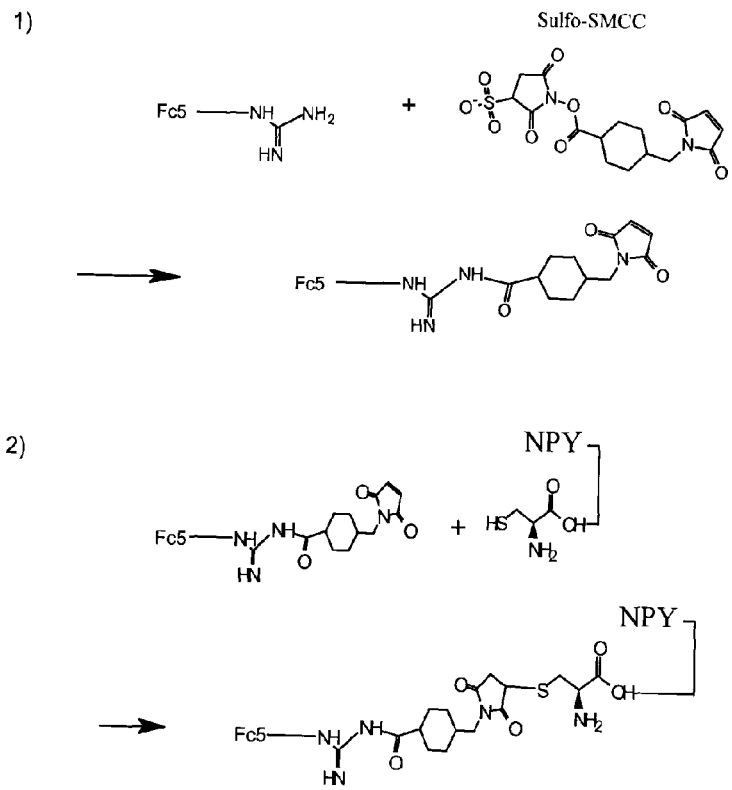
FIG. 14 shows the scheme for chemical synthesis of FC5-neuropeptide Y (NPY). FC5 was first conjugated to the NHS group of Sulfo-SMCC cross-linker (1); then maleimide-activated FC5 (FC5-smcc) was conjugated to reduced NPY-cysteamide (2).

The FC5 sdAb prepared in Example 1 was conjugated to a neuropeptide Y (NPY) fragment (NPY-cys), as described below and shown schematically in FIG. 14.

5 mg of FC5 from Example 1 was placed in a 2-ml microcentrifuge tube. Sulfo-SMCC was added to the FC5 in a 7.5× molar ratio; specifically, 436.4 ul of the 2.5 mg/ml Sulfo-SMCC was added. The micro-centrifuge tube containing the mixture was then flushed with nitrogen gas and incubated for 1 hour at room temperature (RT). Once the reaction was done, the unreacted Sulfo-SMCC was removed from the maleimide-activated FC5 using Pierce 10 ml 7K Zeba column. Prior to sample loading column was washed 3 times with 5 ml PBS and spun at 1000×g for 2 min. After sample loading, the column was completed with 200 µl of PBS and was spun for 2 min at 1000×g.

Separately, and during the above steps, NPY-cysteamide-OH (YPSKPDNPGEDAPAEDMARYYSALRHY-INLITRQRY-cysteamide-OH) was reduced with TCEP. A 5 mg/ml stock of NPY-cys was prepared in 4:1:1 milliQ $H_2O$: acetronitile:methanol and flushed with N2. Similarly, a 25 mM TCEP solution was prepared in $N_2$-flushed milli-Q H2O. 368 µl of the 25 mM TCEP solution was then added to 1444 µl of 5 mg/ml NPY-cys solution to a final concentration of 5 mM. Finally, 18 µl of 0.5M EDTA was added (a final concentration of 5 mM), the solution was then flushed with nitrogen, sealed, vortexed and incubated on ice for 30 min.

The purified maleimide-activated FC5 (2.4 ml) was mixed with the reduced NPY-cys (1.83 ml), flushed with nitrogen, sealed and incubated overnight at 4° C. The next day, the unreacted NPY and the TCEP were removed using Amicon-15 10K column. 10 ml PBS and the sample were added to the column and spun at 4000×g for 7 minutes; volume was reduced to 5 ml; the process was repeated 3 times, the final centrifugation was done for 8 min to reduce the sample to 4 ml. The conjugated sample was then added to a Pierce 10 ml K Zeba column prepared as described above, spun for 2 min at 1000×g and collected.

Figure 15:
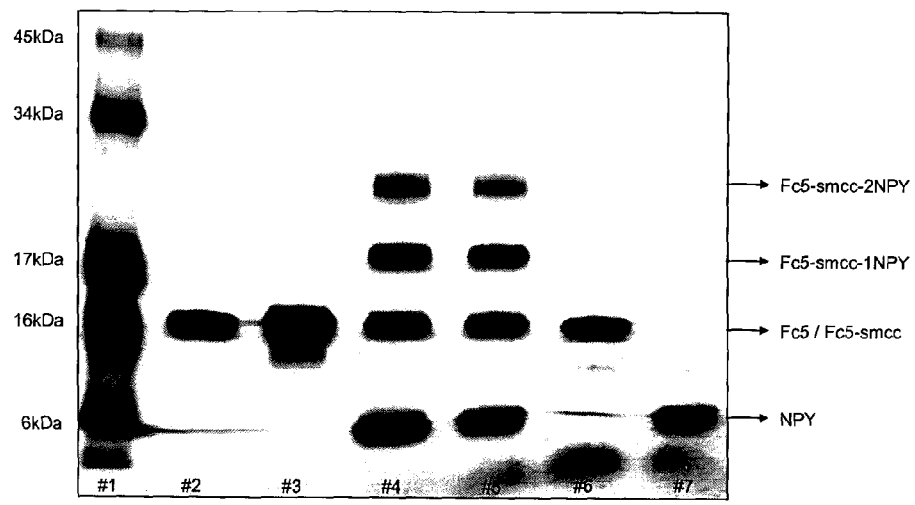
FIG. 15 is a photograph of 16% T-SDS-PAGE, non-reducing silver-stained gel of various components and by-products of reactions described in FIG. 14. Lane #1—molecular weight marker; Lane #2—500 ng FC5; Lane #3—500 ng FC5-SMCC; Lane #4—500 ng FC5-SMCC-NPY before purification; Lane #5—500 ng Fc5-SMCC-NPY after purification; Lane #6—500 ng FC5; Lane #7—500 ng NPY-cys.

Conjugated samples were then run on a 16% T-SDS-PAGE non-reducing gel and silver stained to confirm shift in molecular weight size after conjugation. FIG. 15 shows a photograph of the 16% T-SDS-PAGE of various components and by-products of the reactions. Successful conjugation of FC5 sdAb to NPY-cysteamide (~4.5 kD) is shown. FC5 alone has molecular weight of 15 kD; FC5-NPY conjugates consisted of one NPY molecule per FC5 (MW–20 kD) and 2NPY molecules per FC5 (MW–25 kD).

Example 8

Analgesic Activity of FC5-NPY in Chronic Pain (Paw Flick Assay)

The Paw Flick test described in Example 6 was used to measure the analgesic activity of the FC5-NPY conjugate of Example 7 in chronic pain.

Chronic inflammatory pain was induced in 5-7 weeks old male Wistar rats, by a intra-plantar (i.pl.) injection (100 µl with a 30-gauge needle) of complete Freund's adjuvant in sterile water in a ratio of 1:1 in the right hind paw under brief isoflurane anesthesia (3%). Three days after CFA injection the putative antinociceptive effect of different compounds was quantified by measuring latencies of withdrawal of both hind limb paws (ipsilateral and contralateral to CFA injection) in response to radiant heat using digitalized plantar Analgesia Meter for paw stimulation (IITC Model #336TG Life Science, Inc.). A rapid paw withdrawal on the side of CFA injection (compared to the contralateral non-injected paw) was indicative of inflammatory pain. During the training period (before experiments), the light-intensity lamp was adjusted to elicit baseline paw withdrawal latencies between 17 to 20 s (in rats). If a withdrawal response did not occur within 20 s, the light beam was automatically turned off and the animal was assigned the maximum score. Results were analyzed as temporal courses of paw withdrawal latency (sec) versus time (min or hrs) and expressed as % of maximum possible effect (% MPE) as described in Example 5.

Figure 16:
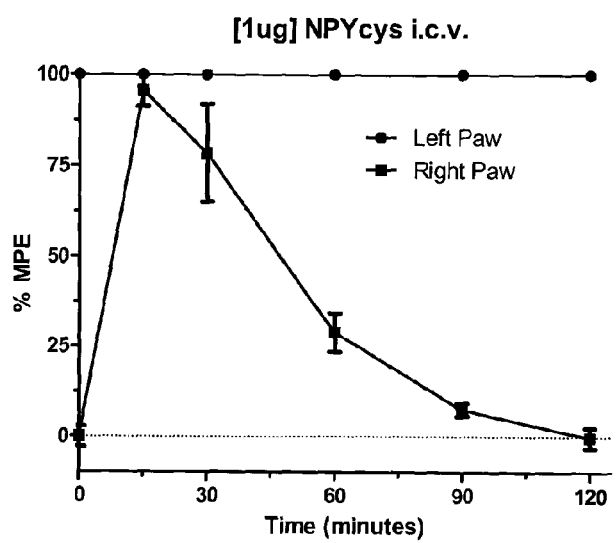
FIG. 16 shows the analgesic effects FC5-NPY (1 μg) after intra-cerebroventricular injection in the paw flick assay (chronic pain model).

Intra-Cerebroventricular Injection:

Rats received 5 µl intra-cerebroventricular injections of NPY (1 µg) as described in Example 6. Results are shown in FIG. 16. The maximum possible analgesic effect was achieved within 15 min of icy injection of NPY, lasted for subsequent 15 min and was then 'washed-out' to basal levels (no analgesia) over following 90 min.

Figure 17:
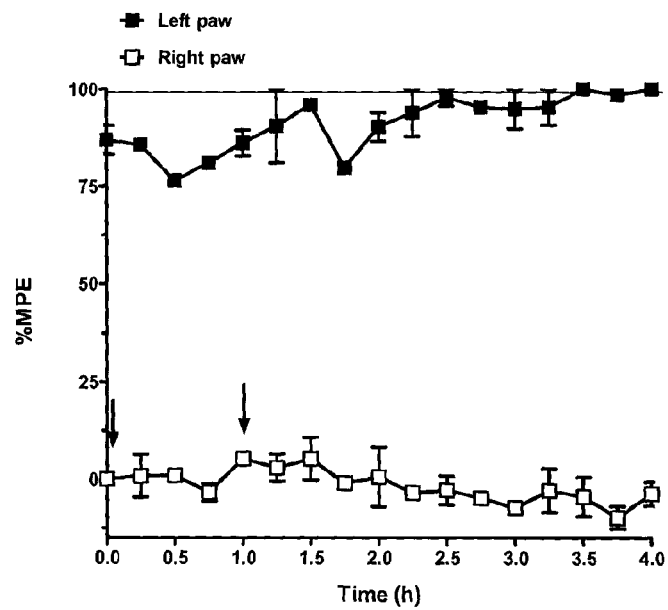
FIG. 17 shows a lack of analgesic effect of NPY after two intravenous injections of 2.02 mg/kg NPY (C-term cysteamide) in each, at 0 h and at 1 h in paw-flick assay (chronic pain model).
Figure 18:
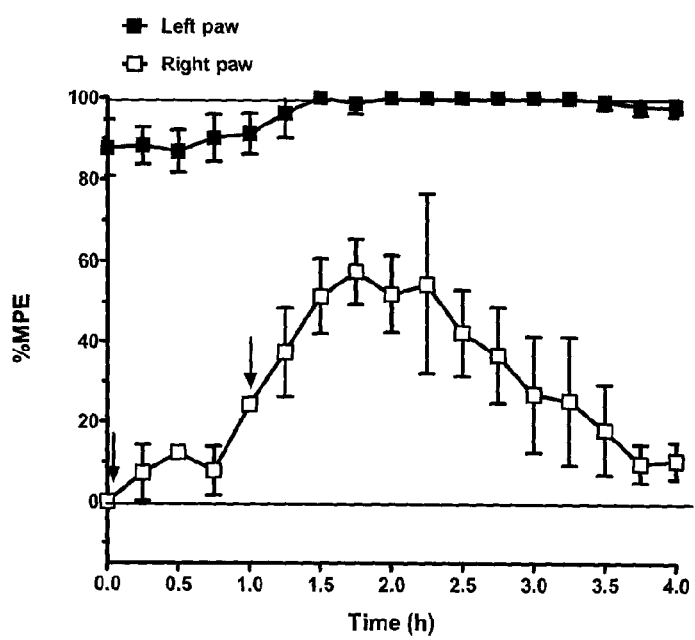
FIG. 18 shows the analgesic effect of the FC5-NPY conjugate after intravenous injections (two injections (5 mg/kg of FC5-NPY in each injection), one at 0 h, one at 1 h) in paw-flick assay (chronic pain model).

Intravenous Injection:

NPY was then injected intravenously in the tail vein in two injections, each containing 2.02 mg/kg of NPY, 1 h apart from each other as described in Example 6. The analgesic effect of NPY was compared to that of FC5-NPY conjugate injected intravenously in two injections 1 h apart, each containing 5 mg/kg (reflecting the dose of NPY received in control experiment). While NPY did not induce any analgesic effect after intravenous administration (FIG. 17), FC5-NPY conjugate demonstrated an analgesic effect reaching 50-60% MPE between 30 min and 1.5 h after injection (FIG. 18). These data demonstrate that neuropeptide Y (NPY), a known analgesic when administered centrally (Munglani et al, 1996) is ineffective when administered peripherally because it does not cross the blood-brain barrier. When NPY was conjugated with the blood-brain barrier 'carrier' single domain antibody, FC5, the conjugate became efficacious in inducing analgesia in chronic pain model because FC5 enabled NPY delivery across the blood brain barrier to the sites of its pharmacological action, central NPY receptors (Balasubramaniam, 1997).

Humans express the same types of analgesia-inducing receptors as rodents; thus, the FC5-NPY construct would be capable of transmigrating the BBB in humans and acting centrally on the NPY receptors of the human brain. Therefore, FC5-NPY conjugate can be used as peripherally-acting non-opioid analgesic for the treatment of chronic pain. Advantageously, this construct does not have typical side-effects of opioid drugs such as morphine.

NPY acts on several types of receptors, of which Y1 receptors are responsible for measured analgesic effect. In addition, NPY has shown anti-epileptogenic effect through Y2 receptors. Antiepileptiform effects of NPY have been demonstrated in hippocampal slice models. Overexpression of NPY in rats renders them resistant to the development of induced seizures (Woldbye et al, 1997; Vezzani et al, 2004). Finally, exogenous NPY application—in vivo via an indwelling cannula or in vitro superfused on acute hippocampal slices—powerfully suppresses various forms of epileptiform activity (Woldbye et al, 1997; Baraban, 2004). This points to anti-epileptic potential of NPYergic agonists in the treatment of complex partial seizures in humans. In the central nervous system, and specifically in hippocampus (an epileptogenic brain region where limbic seizures originate), expression of Y1, Y2 and Y5 are most prominent. Both Y2 and Y5 receptors have been implicated as important 'targets' for developing specific agonists for anti-seizure drugs (Woldbye et al, 1997; Redrobe et al, 1999; Baraban, 2004).

Thus, by virtue of NPY-FC5 being delivered to the brain after systemic injection, as demonstrated by the analgesic effect demonstrated herein, NPY-FC5 could also have other beneficial therapeutic effects mediated via Y receptors, such as treatment for refractory temporal lobe epilepsy, where standard treatments have failed due to developed drug resistance. Similarly, other anti-epiletogenic peptides, such as but not limited to galanin or cortistatin can be delivered across the blood-brain barrier via conjugation to FC5, for action in the brain.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

LIST OF SEQUENCES

FC5

(SEQ ID NO: 10)
GAGGTCCAGCTGCAGGCGTCTGGAGGAGGATTGGTGCAGGCTGGGGG
CTCTCTGAGACTCTCCTGTGCAGCCTCTGGATTCAAAATCACTCACT
ATACCATGGGCTGGTTCCGCCAGGCTCCAGGGAAGGAGCGTGAATTT
GTATCACGTATTACTTGGGGTGGTGATAACACCTTCTATTCAAACTC
CGTGAAGGGCCGATTCACCATTTCCAGAGACAACGCCAAGAACACGG
TCTATCTGCAAATGAACAGCCTGAAACCTGAGGACACGGCCGATTAT
TACTGTGCAGCAGGTTCGACGTCGACTGCGACGCCACTTAGGGTGGA
CTACTGGGGCAAAGGGACCCAGGTCACCGTCTCCTCA (SEQ ID NO: 4)
EVQLQASGGGLVQAGGSLRLSCAASGFKITHYTMGWFRQAPGKEREF
VSRITWGGDNTFYSNSVKGRFTISRDNAKNTVYLQMNSLKPEDTAD
YYCAAGSTSTATPLRVDYWGKGTQVTVSS

TMEM30A isoform 1

(SEQ ID NO: 11)
MAMNYNAKDEVDGGPPCAPGGTAKTRRPDNTAFKQQRLPAWQPILTA
GTVLPIFFIIGLIFIPIGIGIFVTSNNIREIEIDYTGTEPSSPCNKC
LSPDVTPCFCTINFTLEKSFEGNVFMYYGLSNFYQNHRRYVKSRDDS
QLNGDSSALLNPSKECEPYRRNEDKPIAPCGAIANSMFNDTLELFLI
GNDSYPIPIALKKKGIAWWTDKNVKFRNPPGGDNLEERFKGTTKPVN
WLKPVYMLDSDPDNNGFINEDFIVWMRTAALPTFRKLYRLIERKSDL
HPTLPAGRYSLNVTYNYPVHYFDGRKRMILSTISWMGGKNPFLGIAY
IAVGSISFLLGVVLLVINHKYRNSSNTADITI

-continued

TMEM30A isoform 2

(SEQ ID NO: 12)
MAMNYNAKDEVDGGPPCAPGGTAKTRRPDNTAFKQQRLPAWQPILTA
GTVLPIFFIIGLIFIPIGIGIFVTSNNIREIEGNVFMYYGLSNFYQN
HRRYVKSRDDSQLNGDSSALLNPSKECEPYRRNEDKPIAPCGAIANS
MFNDTLELFLIGNDSYPIPIALKKKGIAWWTDKNVKFRNPPGGDNLE
ERFKGTTKPVNWLKPVYMLDSDPDNNGFINEDFIVWMRTAALPTFRK
LYRLIERKSDLHPTLPAGRYSLNVTYNYPVHYFDGRKRMILSTISWM
GGKNPFLGIAYIAVGSISFLLGVVLLVINHKYRNSSNTADITI

TMEM30A isoform 3

(SEQ ID NO: 13)
MYYGLSNFYQNHRRYVKSRDDSQLNGDSSALLNPSKECEPYRRNEDK
PIAPCGAIANSMFNDTLELFLIGNDSYPIPIALKKKGIAWWTDKNVK
FRNPPGGDNLEERFKGTTKPVNWLKPVYMLDSDPDNNGFINEDFIVW
MRTAALPTFRKLYRLIERKSDLHPTLPAGRYSLNVTYNYPVHYFDGR
KRMILSTISWMGGKNPFLGIAYIAVGSISFLLGVVLLVINHKYRNSS
NTADITI

TMEM30A extracellular domain (SEQ ID NO: 14)
GIFVTSNNIREIEIDYTGTEPSSPCNKCLSPDVTPCFCTINFTLEKS
FEGNVFMYYGLSNFYQNHRRYVKSRDDSQLNGDSSALLNPSKECEPY
RRNEDKPIAPCGAIANSMFNDTLELFLIGNDSYPIPIALKKKGIAWW
TDKNVKFRNPPGGDNLEERFKGTTKPVNWLKPVYMLDSDPDNNGFIN
EDFIVWMRTAALPTFRKLYRLIERKSDLHPTLPAGRYSLNVTYNYPV
HYFDGRKRMILSTISWMGGKNP

REFERENCES

All patents, patent applications and publications referred to herein and throughout the application are hereby incorporated by reference in their entirety.

Balasubramaniam A A. (1997) Neuropeptide Y family of hormones: receptor subtypes and antagonists. Peptides. 18(3):445-57.

Baraban S C: Neuropeptide Y and epilepsy: recent progress, prospects and controversies. Neuropeptides 38:261-265, 2004

Bickel, U., Yoshikawa, T., & Pardridge, W. M. Delivery of peptides and proteins through the blood-brain barrier. Adv. Drug Deliv. Rev. 46, 247-279 (2001).

Demeule M, Currie J C, Bertrand Y, Ché C, Nguyen T, Régina A, Gabathuler R, Castaigne J P, Béliveau R. Involvement of the low-density lipoprotein receptor-related protein in the transcytosis of the brain delivery vector angiopep-2. J Neurochem. 106(4):1534-44. (2008)

Eisenberg et al. Analysis of membrane and surface protein sequences with the hydrophobic moment plot. J. Mol. Biol., 179, 125-142.

Garberg P, Ball M, Borg N, Cecchelli R, Fenart L, Hurst R D, Lindmark T, Mabondzo A, Nilsson J E, Raub T J, Stanimirovic D, Terasaki T, Oberg J O, Osterberg T. In vitro models for the blood-brain barrier. Toxicol In Vitro. 19(3): 299-334 (2005).

Hamers-Casterman, C. et al. Naturally occurring antibodies devoid of light chains. Nature 363, 446-448 (1993).

Hervé F, Ghinea N, Scherrmann J M. CNS delivery via adsorptive transcytosis. AAPS J. 10(3):455-72. (2008)

Jespers, L., Schon, O., Famm, K. & Winter, G. Aggregation-resistant domain antibodies selected on phage by heat denaturation. Nat Biotechnol 22, 1161-1165 (2004).

Jones A R, Shusta E V. Blood-brain barrier transport of therapeutics via receptor-mediation. Pharm Res. 24(9):1759-71 (2007)

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147: 1709-19.

Kabat, E. A., Wu, T. T., Perry, H. M, Gottesman, K. S., and Koeler, C. (ed.) (1991) *Sequences of Proteins of Immunological Interest*. US Department of Health and Human Services, US Public Health Service, Bethesda, Md.

Munglani R, Hudspith M J, Hunt S P (1996) The therapeutic potential of neuropeptide Y. Analgesic, anxiolytic and antihypertensive. Drugs. 52(3):371-89.

Murriel C L, Dowdy S F. Influence of protein transduction domains on intracellular delivery of macromolecules. Expert Opin Drug Deliv. 3(6):739-46. (2006)

Muruganandam A, Tanha J, Narang S, Stanimirovic D. Selection of phage-displayed llama single-domain antibodies that transmigrate across human blood-brain barrier endothelium. FASEB J. 16(2):240-2. (2002)

Niederberger E, Kühlein H, Geisslinger G. Update on the pathobiology of neuropathic pain. Expert Rev Proteomics. 5(6):799-818 (2008)

Nuttall, S. D. et al. Isolation and characterization of an IgNAR variable domain specific for the human mitochondrial translocase receptor Tom70. European journal of biochemistry/FEBS 270, 3543-3554 (2003).

Padlan, E. A. Anatomy of the antibody molecule. Molecular immunology 31, 169-217 (1994).

Pardridge, W. M. Drug and gene delivery to the brain: The vascular route. *Neuron* 36:555-558 (2002).

Pardridge, W. M., Buciak, J. L., & Friden, P. M. Selective transport of an anti-transferrin receptor antibody through the blood-brain barrier in vivo. *J. Pharmacol. Exp. Ther.* 259, 66-70 (1991).

Pencheva N, Pospisek J, Hauzerova L, Barth T, Milanov P. Activity profiles of dalargin and its analogues in mu-, delta- and kappa-opioid receptor selective bioassays. Br J Pharmacol. 128(3):569-76 (1999).

Polt R, Dhanasekaran M, Keyari C M. Glycosylated neuropeptides: a new vista for neuropsychopharmacology? Med Res Rev. 25(5):557-85 (2005).

Redrobe J P, Dumont Y, St-Pierre J-A, Quirion R: Multiple receptors for neuropeptide Y in the hippocampus: putative roles in seizures and cognition Brain Research 848:153-166, 1999

Rousselle C, Clair P, Smirnova M, Kolesnikov Y, Pasternak G W, Gac-Breton S, Rees A R, Scherrmann J M, Temsamani J. Improved brain uptake and pharmacological activity of dalargin using a peptide-vector-mediated strategy. J Pharmacol Exp Ther 306(1):371-6 (2003).

Smith H S. Peripherally-acting opioids. Pain Physician. 11(2 Suppl):S121-32. (2008)

To, R. et al. Isolation of monomeric human V(H)s by a phage selection. J Biol Chem 280, 41395-41403 (2005).

Trescot A M, Datta S, Lee M, Hansen H. Opioid pharmacology. Pain Physician. 11(2 Suppl):S133-53 (2008)

Vezzani A, Sperk G: Overexpression of NPY and Y2 receptors in epileptic brain tissue: an endogenous neuroprotective mechanism in temporal lobe epilepsy? Neuropeptides 38: 245-252, 2004.

Weber, S. J., Greene, D. L., Sharma, S. D., Yamamura, H. I., Kramer, T. H., Burks, T. F., Hruby, J. H., Hersh, L. B. and Davis, T. P.: Distribution and antinociception of [³H]cyclic [D-Pen², D-Pen⁵]enkephalin and two halogenated analogs after intravenous administration. J. Pharmacol. Exp. Ther. 259: 1109-1117, 1991

Woldbye D P, Larsen P J, Mikkelsen J D, Klemp K, Madsen T M, Bolwig T G. Powerful inhibition of kainic acid seizures by neuropeptide Y via Y5-like receptors. Nat Med. 3(7):761-4, 1997

Woldbye D P D: Antiepileptic effects of NPY on pentylenetetrazole seizures. Regulatory Peptides 75-76:279-282, 1998

Xapelli S, Agasse F, Ferreira R, Silva A P, Malva J O.: Neuropeptide Y as an endogenous antiepileptic, neuroprotective and pro-neurogenic peptide. Recent Pat CNS Drug Discov.; 1(3):315-24, 2006

WO 2002/057445 (Muruganandam et al).      WO 2007/036021 (Abulrob et al)

U.S. Pat. No. 6,180,370     U.S. Pat. No. 5,693,761     U.S. Pat. No. 6,054,297

U.S. Pat. No. 5,859,205     U.S. Pat. No. 5,869,619     U.S. Pat. No. 5,766,886

U.S. Pat. No. 5,821,123

European Patent No. 626390      European Patent No. 519596

The invention claimed is:

1. A compound comprising a single domain antibody (sdAb) capable of transmigrating across the blood brain barrier (BBB) and an analgesic peptide, wherein the antibody or fragment thereof comprises:
   complementarity determining region (CDR) 1 sequence HYTMG (SEQ ID NO:1);
   CDR2 sequence RITWGGDNTFYSNSVKG (SEQ ID NO:2); and
   CDR3 sequence GSTSTATPLRVDY (SEQ ID NO:3);
wherein the analgesic peptide acts on opioid receptors, neuropeptide Y receptors, neurotensin receptors, galanin receptors, orexin receptors, somatostatin receptors, or any combination thereof.

2. The compound of claim 1, wherein the sdAb comprises the sequence:

```
                                          (SEQ ID NO: 4)
EVQLQASGGGLVQAGGSLRLSCAASGFKITHYTMGWFRQAPGKEREFV

SRITWGGDNTFYSNSVKGRFTISRDNAKNTVYLQMNSLKPEDTADYYC

AAGSTSTATPLRVDYWGKGTQVTVSS,
``` or a sequence at least 95% identical thereto.

3. The compound of claim 1, wherein the analgesic peptide is selected from the group consisting of opioid peptides, endorphins, enkephalins and dynorphins, galanin, neurotensin, neuropeptide Y, somatostatin, orexin A and B, conotoxin-derived peptides, analgesic peptides purified or derived from venoms of scorpion, cone shells, tarantula, or other species.

4. The compound of claim 1, wherein the analgesic peptide is selected from the group consisting of Dalargin and neuropeptide-Y or a fragment thereof.

5. A composition comprising the compound of claim 1 and a pharmaceutically acceptable diluent, carrier, or excipient.

6. A method of treating pain comprising administering the composition according to claim 5 to a subject in need thereof, wherein the composition has anti-nociceptive activity.

7. The method of claim 6, wherein the pain is associated with arthritis, post-operative pain, cancer-related pain, HIV-related pain, or neuropathic pain syndromes.

* * * * *